United States Patent
Hayward et al.

(10) Patent No.: US 6,867,230 B2
(45) Date of Patent: Mar. 15, 2005

(54) HYGROMYCIN A DERIVATIVES

(75) Inventors: Matthew Merrill Hayward, Old Lyme, CT (US); Michael S. Visser, Groton, CT (US); Robert G. Linde, II, Old Lyme, CT (US); Takushi Kaneko, Guilford, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/872,731

(22) Filed: Jun. 1, 2001

(65) Prior Publication Data

US 2003/0045528 A1 Mar. 6, 2003

Related U.S. Application Data

(60) Provisional application No. 60/209,023, filed on Jun. 2, 2000.

(51) Int. Cl.[7] ............... A61K 31/36; C07D 317/66
(52) U.S. Cl. .............. 514/465; 514/23; 514/25; 514/218; 514/233.8; 514/253.11; 514/254.11; 514/316; 514/321; 514/338; 514/397; 514/414; 514/422; 536/16.8; 536/17.9; 536/18.1; 540/575; 544/148; 544/364; 544/377; 546/187; 546/197; 546/283.7; 548/311.7; 548/454; 548/526; 549/435
(58) Field of Search ............ 540/575; 544/364, 544/377, 148; 546/187, 283.7, 326, 197, 526; 548/454, 455, 311.7; 514/218, 253.11, 316, 338, 422, 321, 414, 233.8, 254.11, 465, 397; 549/435

(56) References Cited

U.S. PATENT DOCUMENTS 6,245,745 B1 * 6/2001 Hayward et al. ............ 514/25

FOREIGN PATENT DOCUMENTS

| WO | WO 99/57125 | 11/1999 |
| WO | WO 99/57127 | 11/1999 |
| WO | WO 00/32616 | 6/2000 |
| WO | WO 00/32616 | * 8/2000 |
| WO | WO 01/30795 | 5/2001 |

OTHER PUBLICATIONS

B. H. Jaynes et al., Bioorganic & Medicinal Chemistry Letters, vol. 3, No. 8, pp. 1531–1536, 1993.

* cited by examiner

Primary Examiner—Richard L. Raymond
(74) Attorney, Agent, or Firm—Peter C. Richardson; Gregg C. Benson; Lance Y. Liu

(57) ABSTRACT

This invention relates to compounds of the formula

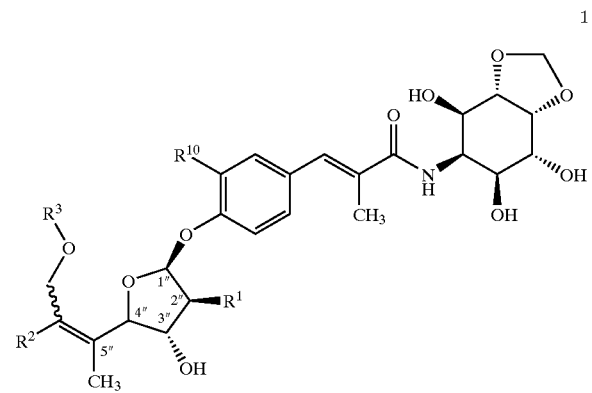

and to pharmaceutically acceptable salts, prodrugs and solvates thereof, wherein $R^1$, $R^2$, $R^3$ and $R^{10}$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1, methods of treating bacterial and protozoal infections by administering the compounds of formula 1.

8 Claims, No Drawings

HYGROMYCIN A DERIVATIVES

BACKGROUND OF THE INVENTION

This application claims priority from U.S. provisional patent application No. 60/209,023, filed Jun. 2, 2000.

This invention relates to novel hygromycin A derivatives that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Hygromycin A is a fermentation-derived natural product first isolated from *Streptomyces hygroscopicus* in 1953. As an antibiotic, hygromycin A possesses activity against human pathogens and is reported to possess potent in vitro activity against *Serpulina* (*Treponema*) *hyodysenteriae* which causes swine dysentery. Several references refer to semisynthetic modifications of hygromycin A, including the following: derivatization of the 5" ketone of hygromycin A to the 2,4-dinitrophenylhydrazone is referred to in K. Isono et al., *J. Antibiotics* 1957, 10, 21, and R. L. Mann and D. O. Woolf, *J. Amer Chem. Soc.* 1957, 79, 120. K. Isono et al., ibid., also refer to the thiosemicarbazone at 5"; reduction of the 5" ketone of hygromycin A to the 5" alcohol is referred to in R. L. Mann and D. O. Woolf, ibid., as well as in S. J. Hecker et al., *Bioorg. Med. Chem. Left.* 1992, 2, 533 and S. J. Hecker et al., *Bioorg. Med. Chem. Left.* 1993, 3, 295; furanose analogues are referred to in B. H. Jaynes et al., *Bioorg. Med. Chem. Left.* 1993, 3, 1531, and B. H. Jaynes et al., *J. Antibiot.* 1992, 45, 1705; aromatic ring analogues are referred to in S. J. Hecker et al., *Bioorg. Med. Chem. Left.* 1993, 3, 289, and C. B. Cooper et al., *Bioorg. Med. Chem. Left.* 1997, 7, 1747; enamide analogues are referred to in S. J. Hecker et al., *Bioorg. Med. Chem. Left.* 1992, 2, 533; aminocyclitol analogues are referred to in S. J. Hecker et al., *Bioorg. Med. Chem. Left.* 1992, 2, 1015, and in S. J. Hecker et al., *Bioorg. Med. Chem. Left.* 1992, 2, 1043. The hygromycin A derivatives of the present invention possess broad activity against both gram-negative and gram-positive bacteria and protozoa. Hygromycin derivatives are also described and claimed in U.S. provisional patent application No. 60/162,581 (filed Oct. 29, 1999) and U.S. patent application Ser. Nos. 09/462,592 (filed May 3, 1999), 09/380,718 (filed Apr. 8, 1999), and 09/453,429 (filed Dec. 2, 1999); the foregoing United States provisional application and utility patent applications are incorporated herein by reference in their entirety.

SUMMARY OF THE INVENTION

The present invention relates to compounds of the formula 1

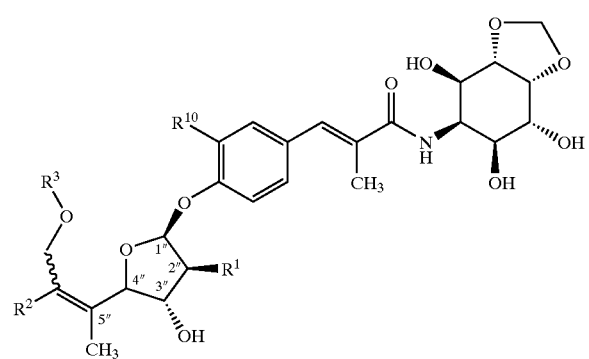

and to pharmaceutically acceptable prodrugs, salts and solvates thereof wherein:

each $R^1$ and $R^{10}$ is independently H or OH;

$R^2$ is H or $C_1$–$C_6$ alkyl wherein the foregoing $R^2$ alkyl group is optionally substituted by 1 or 2 $R^4$ groups;

each $R^3$ is independently selected from $C_6$–$C_{10}$ aryl or 5 to 10 membered heteroaromatic, and the heteroaromatic and aryl moieties of the foregoing $R^3$ groups are substituted by a —$CHR^9NR^{11}R^{12}$group and optionally substituted by 1 to 4 $R^4$ groups;

each $R^4$ is independently selected from, $C_1$–$C_{10}$ alkyl, $C_2$–$C_{10}$ alkenyl, $C_2$–$C_{10}$ alkynyl, halo, cyano, nitro, trifluoromethyl, difluoromethyl, trifluoromethoxy, azido, hydroxy, $C_1$–$C_6$ alkoxy, —$C(O)R^5$, —$C(O)OR^5$, —$NR^6C(O)OR^8$, —$OC(O)R^5$, —$NR^6SO_2R^8$, —$SO_2NR^5R^6$, —$NR^6C(O)R^5$, —$C(O)NR^5R^6$, —$NR^5R^6$, —$S(O)_j(CR^6R^7)_m(C_6$–$C_{10}$ aryl), —$S(O)_j(C_1$–$C_6$ alkyl), —$(CR^6R^7)_m(C_6$–$C_{10}$ aryl), —$O(CR^6R^7)_m(C_6$–$C_{10}$ aryl), —$NR^6(CR^6R^7)_m(C_6$–$C_{10}$ aryl), —$(CR^6R^7)_m$(4 to 10 membered heterocyclic), —$C(O)(CR^6R^7)_m(C_6$–$C_{10}$ aryl), and —$C(O)(CR^6R^7)_m$(4 to 10 membered heterocyclic), wherein m is an integer from 0 to 4; j is an integer from 0 to 2, and said alkyl, alkenyl, alkynyl, aryl and heterocyclic moieties of the foregoing $R^4$ groups are optionally substituted by 1 to 3 substituents independently selected from halo, cyano, nitro, trifluoromethyl, trifluoromethoxy, azido, —$NR^6SO_2R^8$, —$SO_2NR^5R^6$, —$C(O)R^5$, —$C(O)OR^5$, —$OC(O)R^5$, —$NR^6C(O)OR^8$, —$NR^6C(O)R^5$, —$C(O)NR^5R^6$, —$NR^5R^6$, —$OR^5$, $C_1$–$C_{10}$ alkyl, —$(CR^6R^7)_m(C_6$–$C_{10}$ aryl), and —$(CR^6R^7)_m$(4 to 10 membered heterocyclic), wherein m is an integer from 0 to 4;

each $R^5$, $R^9$, $R^{11}$, $R^{12}$, $R^{13}$ and $R^{14}$ is independently selected from H, $C_1$–$C_{10}$ alkyl, —$(CR^6R^7)_m(C_6$–$C_{10}$ aryl), —$(CR^6R^7)_m(C_3$–$C_{10}$ cycloalkyl), indanyl and —$(CR^6R^7)_m$(4 to 10 membered heterocyclic), wherein m is an integer from 0 to 4, and the foregoing $R^5$, $R^{11}$, $R^9$ and $R^{12}$ substituents, except H, are optionally substituted by 1 to 3 substituents independently selected from halo, cyano, nitro, benzyl, trifluoromethyl, trifluoromethoxy, azido, —$CH_2$($C_2$–$C_6$ alkenyl), —$C(O)R^6$, —$C(O)OR^6$, —$OC(O)R^6$, —$NR^6C(O)R^7$, —$C(O)NR^6R^7$, —$NR^6R^7$, hydroxy, $C_1$–$C_6$ alkyl, and $C_1$–$C_6$ alkoxy;

or $R^{11}$ and $R^{12}$ can be taken together to form a 4 to 7 membered heterocyclic group optionally substituted by one $R^{14}$ group;

each $R^6$ and $R^7$ is independently selected from H, —$C(O)$($C_1$–$C_6$ alkyl), $C_1$–$C_6$ alkyl or —$(CH_2)_n(C_6$–$C_{10}$ aryl) wherein n is an integer from 0 to 2, and the foregoing aryl substituents are optionally substituted by 1 to 3 substituents independently selected from halo, cyano, nitro, trifluoromethyl, trifluoromethoxy, and azido;

—$NR^6R^7$ can be taken together to form the following structure

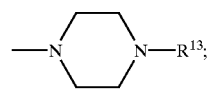

each $R^8$ is selected from the substituents provided in the definition of $R^5$ except $R^8$ is not H.

Specific embodiments of said compounds of formula 1 include those wherein $R^3$ is phenyl substituted by one —$CH_2NR^{11}R^{12}$ group and optionally substituted by 1 to 4 $R^4$ groups. In a more specific embodiment, said phenyl group is substituted by one —$CH_2NR^{11}R^{12}$ group and one of the $R^4$ groups is halo and ortho to the ether oxygen. In an even more specific embodiment said halo group is chlorine.

Specific embodiments of said compounds of formula 1 include those wherein $R^3$ is phenyl optionally substituted by 1 to 4 $R^4$ groups and substituted by one —$CH_2NR^{11}R^{12}$ group wherein said $R^{11}$ and $R^{12}$ groups are independently selected from $C_1$–$C_{10}$ alkyl, —$(CR^6R^7)_m$($C_6$–$C_{10}$ aryl), —$(CR^6R^7)_m$($C_3$–$C_{10}$ cycloalkyl), indanyl and —$(CR^6R^7)_m$ (4 to 10 membered heterocyclic), wherein m is an integer from 0 to 4, and the foregoing, $R^{11}$ and $R^{12}$ substituents, are optionally substituted by 1 to 3 substituents independently selected from halo, benzyl, trifluoromethyl, trifluoromethoxy, —$NR^6R^7$. In a more specific embodiment, said phenyl group is substituted by one —$CH_2NR^{11}R^{12}$group and one of the $R^4$ groups is halo and ortho to the ether oxygen. In an even more specific embodiment said halo group is chlorine.

Specific preferred compounds of formula 1 include those selected from the group consisting of:

3-(4-{(2S,3S,4S,5R)-5-[3-{2-chloro-4-[(methyl-napthalen-1-ylmethyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-benzylaminomethyl-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(-{(2S,4S,5R)-5-[3-(4-{[Benzyl-(2-dimethylamino-ethyl)-amino]-methyl}-2-chloro-phenoxy)-1-methyl-(1E)-propenyl]-4-hydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide 3-(4-{(2S,3S,4S,5R)-5-[3-(2,3-Dichloro-4-{[(3-dimethylamino-propyl)-ethyl-amino]-methyl}-phenoxy)-1-methyl-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide 3-(4-{(2S,3S,4S,5R)-5-[3-(4-(3-chloro-benzyl)aminomethyl-2-chloro-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-ethylamino-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(3-piperidinyl-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-benzylaminomethyl-2-chloro-phenoxy)-1-methyl-(1E)-propenyl]-4-hydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl )-(2E)-acrylamide;

3-(4-{(2S,3S,4S,5R)-5-[3-{2-chloro-4-[(benzyl-methyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-{2-chloro-4-[(ethyl-methyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-{2-chloro-4-morpholin-4ylmethyl-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-(3-chloro-benzyl)aminomethyl-2-chloro-phenoxy)-1-methyl-(1E)-propenyl]-3,4-dihydroxy-tetrahydro-furan-2-yloxy}-phenyl)-2-methyl-N-((3aS,4R,5R,6S,7R,7aR)-4,6,7-trihydroxy-hexahydro-benzo[1,3]dioxol-5-yl)-(2E)-acrylamide;

and the pharmaceutically acceptable salts, solvates and prodrugs of said compounds.

The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula 1, or a pharmaceutically acceptable salt thereof, and a pharmaceutically acceptable carrier.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula 1 or a pharmaceutically acceptable salt thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chiamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C-F (minute-colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative *staphylococcal* species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or *Bordetella* spp.; cow enteric disease related to infection by *E. coli* or protozoa (i.e., coccidia, cryptosporidia, etc.); dairy cow mastitis related to infection by *S. aureus, Strep. uberis, Streptococcus agalactiae, Streptococcus dysgalactiae, Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodysinteriae*; cow footrot related to infection by *Fusobacterium* spp.; cow metritis related to infection by *E coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The compounds of the present invention may be active against the bacteria and protoazoa, and associated conditions, referred to above, or specific strains of the bacteria and protozoa referred to above.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for said alkyl group to include cyclic moieties it must contain at least three carbon atoms.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached). The term "5 to 10 membered heteroaromatic" is defined in accord with the portions of the above definition related to aromatic groups.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations of the —CH$_2$OR$^3$ moiety. The compounds of formula 1 may also exist as tautomers. This invention relates to the use of all such tautomers and mixtures thereof.

The subject invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Selective introduction of prodrug side chains can be carried out on the hydroxy groups of the hygromycin A core molecule. For instance, exhaustive silylation of the six hydroxy groups of hygromycin A can be carried out, for instance with tert-butyl dimethylsilyl chloride. Subjection of the hexasilyl derivative to the action of potassium carbonate in methanol at room temperature selectively removes the phenolic silyl group, allowing further selective modification at that position. In another example, incomplete silylation of hygromycin A provides the pentasilyl derivative in which the C-2" hydroxy group of the furanose ring is free. Selective acylation, alkylation, etc. can be carried out on this derivative to provide prodrug attachment at C-2", followed by elaboration to the compounds of formula 1.

DETAILED DESCRIPTION OF THE INVENTION

The preparation of the compounds of the present invention is illustrated in the following Scheme.

Scheme

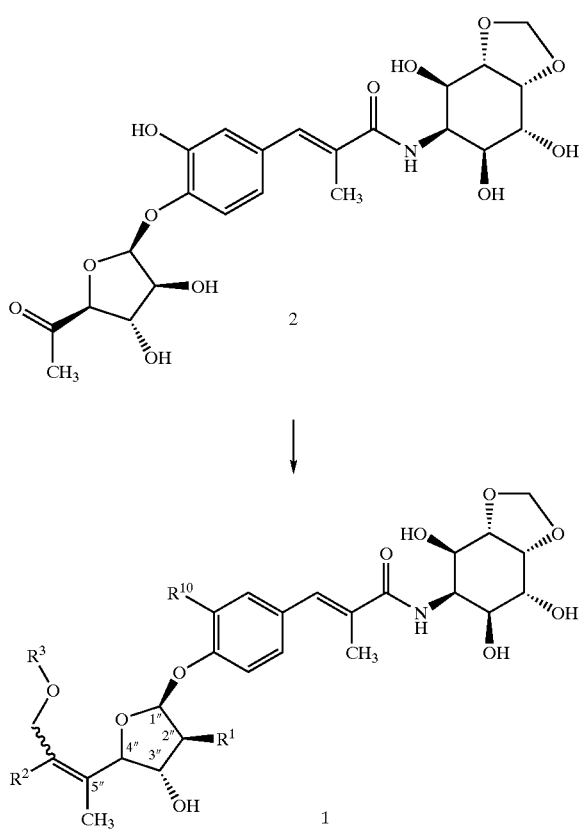

The compounds of the present invention are readily prepared. With reference to the Scheme illustrated above, the starting compound of formula 2 is hygromycin A which may be prepared according to procedures known to those skilled in the art, such as by fermentation of *Streptomyces hygroscopicus* NRRL 2388. The methyl ketone at 4" on the furanose sugar of the hygromycin A molecule can exist in the S configuration (hygromycin A) or R configuration (epi-hygromycin) on the furanose sugar. When published protocols are used as a model for fermentation and recovery of hygromycin A (U.S. Pat. No. 3,100,176; Antibiotic Chemotherapy (1953)3:1268–1278, 1279–1282), the hygromycin product is an approximately 3:1 mixture of hygromycin A (the 4"-(S) epimer), with the beta-oriented methyl ketone on the furanose sugar, as drawn, and epi-hygromycin. It is known in the literature (Journal of Antibiotics 33(7), 695–704, 1980) that pure hygromycin A will convert to epi-hygromycin in alkaline solutions. By carefully controlling the pH below 6.9 during the fermentation, and the pH, temperature and solvent exposure during the purification process, the final recovered product may be improved to at least a 14:1 ratio of hygromycin A: epi-hygromycin. Using this material, substantially single isomers derived from the 4"-(S) hygromycin may be prepared for use as templates for further synthetic modification.

Hygromycin A enriched for the 4"-(S) epimer is produced by fermentation of *Streptomyces hygroscopicus* NRRL2388, or mutants thereof, in media with pH controlled at less than 6.9, preferably 6.2 to 6.7, throughout the process. The medium contains assimilable sources of carbon, nitrogen and trace elements, as known to those skilled in the art. The fermentation is run at a temperature of about 25–35° C., preferably about 29° C. The fermentation is monitored, for example by high pressure liquid chromatography. Incubation is continued until the yield of the compound reaches a maximum, generally for a period of about 3 to 10 days, preferably about 4 to 6 days.

The formation of epi-hygromycin is minimized during the purification process by using an aqueous buffer (rather than unbuffered water) and controlling the pH of the active streams to near 6.0. Epi-hygromycin formation is also minimized by minimizing the time the recovered material is subject to higher temperatures. Thus, where it is necessary to reduce solvent concentrations, it is preferred to dilute active streams with the aqueous buffer and avoid use of rotary evaporation at elevated temperatures. Also, as means of avoiding higher temperatures, a resin column may be used to concentrate the active solution prior to the final purification step in order to reduce the volume of solution that must be boiled. The final purification step in the process is the concentration of the active cuts to solids using vacuum and a bath temperature of about 35–50° C. The period in which the solution is subject to elevated temperatures may be minimized by boiling in stages.

The compound of formula 1 where $R^2$ and $R^3$ are defined as above, $R^1$ is OH and $R^{10}$ is OH may be prepared through the corresponding α,β-unsaturated ester intermediates derived from Wittig, Horner-Emmons or Peterson olefination of the C-5" ketone of hygromycin A. For instance, (carbethoxymethylene)triphenylphosphorane or (carbethoxyethylidene)triphenyl-phosphorane can be reacted with hygromycin A to provide the unsaturated ethyl ester. At this point the hydroxy groups of hygromycin A may be appropriately protected, for instance as their silyl ethers using an appropriate reagent such as triethylsilyl chloride (TESCI), trimethylsilyl chloride (TMSCI) or tert-butyldimethylsilyl chloride (TBDMSCI) and an amine base, such as imidazole or pyridine. This compound may then be reduced, for instance with diisobutyl aluminum hydride. The ether can then be prepared via a Mitsunobu reaction. The protected hygromycin allyl alcohol is subjected to a Mitsunobu reaction with HO—$R^3$ mediated by triphenylphosphine and diethyl azodicarboxylate as described in D. L. Hughes, Org. Reactions (1992) 42 335. Deprotection of the hydroxyl groups may be carried out by use of acid, such as acetic acid or fluoride ion, such as TBAF or with a complex of hydrofluoric acid and pyridine.

The compound of formula 1 where $R^2$ and $R^3$ are defined as above, $R^1$ is H and $R^{10}$ is OH can be prepared through the corresponding α,β-unsaturated ester intermediates derived from Wittig, Horner-Emmons or Peterson olefination of the C-5" ketone of 2"-deoxy-pentaprotected hygromycin A. In this process pentasilylhygromycin A is prepared by protection of all of the hydroxy groups of hygromycin A, with the exception of the hydroxy at the 2" carbon (C-2"), as their silyl ethers using an appropriate reagent such as triethylsilyl chloride (TESCI), trimethylsilyl chloride (TMSCI) or tert-butyldimethysilyl chloride (TBDMSCI). The preferred method is 10 eq of TBDMSCI and imidazole in N,N-dimethylformamide (DMF) at a temperature of 25–40° C. for 12–36 hours. The 2"-deoxy-pentaprotected hygromycin A is then prepared by removal of the hydroxy group using the method of Barton et al., *J. Chem Soc., Perkin Trans. I* 1975, 1574. The preferred method in this case is the method of Génu-Dellac et al., *Carbohydrate Res.* 1991, 216, 249. The aforementioned α,β-unsaturated ester may then be prepared via a Wittig, Horner-Emmons or Peterson olefination of the C-5" ketone of 2"-deoxy-pentaprotected hygromycin A. For instance, (carbethoxymethylene)

triphenylphosphorane or (carbethoxyethylidene)triphenylphosphorane can be reacted with hygromycin A to provide the unsaturated ethyl ester. This compound may then be reduced, for instance with diisobutyl aluminum hydride. The protected 2"-deoxyhygromycin allyl alcohol is subjected to a Mitsunobu reaction with HO—$R^3$ mediated by triphenylphosphine and diethyl azodicarboxylate as described in D. L. Hughes, Org. Reactions (1992) 42 335. Deprotection of the hydroxyl groups may be carried out by use of acid, such as acetic acid or fluoride ion, such as TBAF or with a complex of hydrofluoric acid and pyridine.

The compound of formula 1 where $R^2$ and $R^3$ are defined as above, $R^1$ is OH and $R^{10}$ is H can be prepared through the corresponding α,β-unsaturated ester intermediates derived from Wittig, Horner-Emmons or Peterson olefination of the C-5" ketone of 3-deoxy-hygromycin A. In this process 3-deoxy-hygromycin A is prepared by reacting hygromycin A, with N-phenyl-bis(trifluoromethanesulphonamide) in the presence of a hindered base such as triethyl amine in a polar aprotic solvent such as N,N-dimethylformamide at room temperature for 1–4 h. Treatment of the resultant phenyl triflate with formic acid and triethyl amine in the presence of a palladium catalyst such as tris(dibenzylidineacetone)dipalladium(0)-chloroform adduct and a ligand such as 1,1'-bis(diphenylphosphino)ferrocene in a polar aprotic solvent such as N,N-dimethylformamide at 35–70° C. for 10–24 h provides the 3-deoxy-hygromycin A. The aforementioned α,β-unsaturated ester may then be prepared via a Wittig, Horner-Emmons or Peterson olefination of the C-5" ketone of 2"-deoxy-pentaprotected hygromycin A. For instance, (carbethoxymethylene)triphenylphosphorane or (carbethoxyethylidene)triphenyl-phosphorane can be reacted with hygromycin A to provide the unsaturated ethyl ester. This compound may then be reduced, for instance with diisobutyl aluminum hydride. The protected 3-deoxyhygromycin allyl alcohol is subjected to a Mitsunobu reaction with HO—$R^3$ mediated by triphenylphosphine and diethyl azodicarboxylate as described in D. L. Hughes, Org. Reactions (1992) 42 335. Deprotection of the hydroxyl groups may be carried out by use of acid, such as acetic acid or fluoride ion, such as TBAF or with a complex of hydrofluoric acid and pyridine.

The compound of formula 1 where $R^2$ and $R^3$ are defined as above, $R^1$ is H and $R^{10}$ is H can be prepared through the corresponding α,β-unsaturated ester intermediates derived from Wittig, Horner-Emmons or Peterson olefination of the C-5" ketone of 2",3-dideoxy-hygromycin A. In this process 3-deoxy-hygromycin A is prepared as above. Tetrasilyl-3-deoxyhygromycin A is prepared by protection of all of the hydroxy groups of 3-deoxyhygromycin A, with the exception of the hydroxy at the 2" carbon (C-2"), as their silyl ethers using an appropriate reagent such as triethylsilyl chloride (TESCI), trimethylsilyl chloride (TMSCI) or tert-butyldimethysilyl chloride (TBDMSCI). The preferred method is 10 eq of TBDMSCI and imidazole in N,N-dimethylformamide (DMF) at a temperature of 25–40° C. for 12–36 hours. The 2",3-dideoxy-tetraprotected hygromycin A is then prepared by removal of the hydroxy group using the method of Barton et al., *J. Chem Soc., Perkin Trans. I* 1975, 1574. The preferred method in this case is the method of Génu-Dellac et al., *Carbohydrate Res.* 1991, 216, 249. The aforementioned α,β-unsaturated ester may then be prepared via a Wittig, Horner-Emmons or Peterson olefination of the C-5" ketone of 2",3-dideoxy-tetraprotected hygromycin A. For instance, (carbethoxymethylene) triphenylphosphorane or (carbethoxyethylidene)triphenylphosphorane can be reacted with 2",3-dideoxy-tetraprotected hygromycin A to provide the unsaturated ethyl ester. This compound may then be reduced, for instance with diisobutyl aluminum hydride. The protected 2",3-dideoxyhygromycin allyl alcohol is subjected to a Mitsunobu reaction with HO—$R^3$ mediated by triphenylphosphine and diethyl azodicarboxylate as described in D. L. Hughes, Org. Reactions (1992) 42 335. Deprotection of the hydroxyl groups may be carried out by use of acid, such as acetic acid or fluoride ion, such as TBAF or with a complex of hydrofluoric acid and pyridine.

An alternative method of preparation of compounds of the formula 1 is to subject the appropriate allyl alcohol intermediates described above to a Mitusnobu reaction with HO—$R^3$ wherein said HO—$R^3$ contains an aldehyde or ketone ($R^9C=O$) in place of the $CHR^9NR^{11},R^{12}$ substutuent. Deprotection of the hydroxyl groups may be carried out by use of acid, such as acetic acid or fluoride ion, such as TBAF or with a complex of hydrofluoric acid and pyridine. Formation of the $CHR^9NR^{11},R^{12}$ substituent may be achieved by reductive amination using an amine of formula $HNR11,R^{12}$ and sodium triacetoxy borohydride, sodium cyanoborohydride or a polymer bound cyanoborohydride such as (polystyrylmethyl)triethylammonium cyanoborohydride in a solvent such as THF or DMF for 3–24 h at a temperature of 20–70° C.

Amines of formula $HNR11,R^{12}$ and compounds of the formula HO—$R^3$ including those containing an aldehyde or ketone ($R^9C=O$) in place of the $CH_2NR11,R^{12}$ can be prepared by those skilled in the art.

The compounds of the present invention have asymmetric carbon atoms. Compounds having a mixture of isomers at one or more centers will exist as diastereomeric mixtures, which can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case, stoichiometric quantities of reagents are preferably employed in order to ensure completeness of reaction and maximum yields of the desired final product.

The antibacterial activity of the compounds of the present invention against bacterial pathogens is demonstrated by the compound's ability to inhibit growth of defined strains of pathogens.

Assay

The assay, described below, employs conventional methodology and interpretation criteria and is designed to provide direction for chemical modifications that may lead to compounds with antibacterial activity against susceptible and drug-resistant organisms including, but not limited to, beta-lactam, macrolide and vancomycin resistance. In the assay, a panel of bacterial strains is assembled to include a variety of target pathogenic species, including representatives of antibiotic resistant bacteria. Use of this panel enables the chemical structure/activity relationship to be determined with respect to potency and spectrum of activity. The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

The activity of the compounds of the present invention also may be assessed in accord with Steers replicator technique which is a standard in vitro bacterial testing method described by Steers et al., *Antibiotics and Chemotherapy* 1959, 9, 307.

The in vivo activity of the compounds of the present invention can be determined by conventional animal protection studies well known to those skilled in the art, usually carried out in rodents.

According to one in vivo model, compounds are evaluated for efficacy in mouse models of acute bacterial infection. An example of one such in vivo system is provided as follows. Mice (CF1 mixed sex mice; 18–20 g) are allotted to cages upon their arrival, and allowed to acclimate 1–2 days before being placed in a study. The acute infection is produced by intraperitoneal inoculation of bacteria (*Staphylococcus aureus* strain 01A1095) suspended in 5% sterile hog gastric mucin. The inoculum is prepared by: growing the culture overnight at 37° C. on blood agar, harvesting the resulting surface growth with sterile brain heart infusion broth, and adjusting this suspension to a turbidity that when diluted 1:10 into 5% sterile hog gastric mucin would produce 100% lethality.

Mice (10 per group) are treated subcutaneously, at 0.5 hour and 4 hours after challenge. Appropriate non-treated (infected but not treated) and positive (vancomycin or minocycline, etc.) controls are included in each study. Percent survival is recorded after a 4-day observation period; the $PD_{50}$ (mg/kg/dose calculated to protect 50% of infected animals) is determined by the probit method.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 3 mg/kg/day to about 60 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous ethanol or propylene glycol may be employed. Use of a cyclodextrin derivative such as β-cyclodextrin sulfobutyl ether, sodium salt (see U.S. Pat. No. 5,134,127) may also be advantageous. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is further described and exemplified in the preparations and examples described below. In the preparations and examples, "rt" means room or ambient temperature which is a temperature within the range of about 20–25° C., THF means tetrahydrofuran (and other commonly used solvents are referred to by those acronyms or abbreviations familiar to those skilled in the art), "min" means minute(s), "Me" means methyl, "Et" means ethyl, "Ac" means acetyl, and "h" and "hrs" mean hour(s).

Preparation 1

Five (5) mL of a frozen lot (stored at −80° C. in 20% glycerol/80% inoculum medium) of the culture *Streptomyces hygroscopicus* NRRL 2388 was used to inoculate 1 L of hygromycin inoculum medium (Corn Products Corp. cerelose 13 g/L, Hubinger starch 7 g/L, Roquette corn steep solids 3 g/L, Sheffield Brand Products NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 3 days at 29° C. with 200 rpm agitation on a 2-inch-throw shaker. This grown culture was used to inoculate 8L of sterile hygromycin fermentation medium (Albaglos calcium carbonate 1 g/L, Sheffield Brand Products NZ Amine YTT 5 g/L, Hubinger's starch 20 g/L, Archer Daniels Midland Nutrisoy flour 10 g/L, Dow Chemical P2000 defoamer 1 ml/L, Baker $CoCl_2.6H_2O$ 0.002 g/L, Colfax soybean oil 2 ml/L, cerelose 10 g/L, NaCl 5 g/L, pH to 7.0 before autoclave) in a 14 liter fermentor jar (New Brunswick Microferm, New Brunswick, N.J.) equipped with two 4.75-inch Rushton impellers, spaced 3.75 inches from each other. The broth was incubated at 29° C. with an aeration rate of 8 L/minute, and with stirring at 800 rpm. To minimize formation of epi-hygromycin, the pH was maintained between 6.5 and 6.9 for 126 hours, then to 6.2 to 6.6 with $H_2SO_4$ (15%) for the rest of the run. The fermentation was harvested after 143 hours total incubation. At this time, the ratio was 31:1 hygromycin A to epi-hygromycin.

Six liters of broth from the above fermentation was centrifuged at 8000 rpm for approximately 15 minutes. After centrifugation, the pellet was discarded and the supernatant (at pH 6.4, assayed by HPLC to contain approximately 4.12 gms of hygromycin A activity) was loaded on a column packed with 500 gms of an XAD-16 resin (Rohm and Haas (Philadelphia, Pa.). The resin had previously been equilibrated with two bed volumes of 25 mM di-sodium phosphate, pH 6.0 ("buffer"). After loading, the column was washed with 2 bed volumes of buffer and 2 bed volumes of 80/20 buffer/methanol and the activity eluted with 5 bed volumes of 50/50 buffer/methanol. The cuts were assayed by HPLC and the cuts containing the bulk of the activity (2.730 gms of hygromycin A) were combined.

A part of this XAD-16 eluate (approximately 800 mg of hygromycin A) was diluted to 10% methanol by the addition of 1.8 liters of buffer and loaded on a 100 ml CG-161 column (TosoHaas (Montgomeryville, Pa.)) which had been equilibrated with 4 bed volumes of 90/10 buffer/methanol. The product was eluted with 6 bed volumes of 50/50 buffer/methanol. The cuts were assayed by HPLC and the active cuts were combined. The combined cut was evaporated to dryness and the solids assayed to be approximately 65% pure by weight. A small part of these solids were transferred for assay.

About 500 mg of the solids were mixed with 500 ml of water and 500 ml of ethyl acetate and stirred for 20 minutes. The two layers were separated and part of the aqueous layer was dried to obtain solids which were assayed to be approximately 52% purity by weight. Both these solids (#34945-280-1 and 281-1) were assayed by NMR and TLC and found to contain hygromycin A activity. In addition, the NMR showed a hygromycin A/epi-hygromycin ratio of approximately 15:1.

Preparation 2

Five (5) mL of a frozen lot (stored at −80° C. in 20% glycerol/80% inoculum medium) of the culture *Streptomyces hygroscopicus* NRRL 2388 was used to inoculate 1L of Hygromycin inoculum medium (CPC International Inc. cerelose 13 g/L, Hubinger's starch 7 g/L, Roquette corn steep solids 3 g/L, NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 2 to 3 days at 29° C. with 200 rpm agitation on a 2-inch-throw shaker. Two five-hundred gallon, stainless steel fermentors were loaded with 380–400 gallons of the hygromycin fermentation medium (Mineral Technologies Calcium Carbonate 1 g/L, Sheffield Brand Products NZ Amine YTT 5 g/L, Hubinger's starch 20 g/L, Archer Daniels Midland Co., Soyflour 10 g/L, Dow Chemical P2000 defoamer 1 ml/L, Baker $CoCl_2.6H_2O$ 0.002 g/L, Colfax, Inc. soybean oil 2 gm/L, CPC International Inc. Cerelose 10 g/L, Cargill Inc. NaCl 5 g/L,). The medium was sterilized with 20 psig of steam for 60 minutes in the fermentors. After the medium was cooled using cooling coils in the fermentors, the pH was adjusted to 6.5–6.7. The fermentor conditions were set so that the airflow rate was 20 standard cubic feet per minute, the temperature was 28° C., the vent pressure was 5 psig, and the pH was maintained between 6.5–6.7 with 25% sodium hydroxide and 98% sulfuric acid. The agitation rates in the two fermentors were varied so as to maintain a dissolved oxygen level of greater than 20% of saturation level as measured in the broth immediately prior to inoculation. Upon setting the fermentor control conditions, five Fernbach inoculum flasks were combined in a sterile manner, into an 8 L aspirator bottle. This inoculum was then used for inoculation of a single, nominal, five-hundred gallon fermentor as described above. This procedure was repeated using 4 liters of inoculum so that one fermentor received four liters of inoculum and one fermenter received five liters of inoculum. Each fermentor ran for approximately 114 hours, at which time the fermentations were stopped. The broth pH was adjusted to 6.3 using 98% sulfuric acid and transferred from the fermentors for recovery.

The two fermentors referred to above (pH=6.3, having a ratio of hygromycin A to epi-hygromycin of approximately 51:1) were filtered on a ceramic filtration system. The filtrate (1450 gmsA, 506 gal) was loaded on a 70-gallon XAD-16 resin column. This column had been equilibrated previously with 4 bed volumes of a solution of trisodium phosphate buffer at pH 6.0 ("buffer"). After loading, the column was washed with 2 bed volumes of buffer and 2 bed volumes of 80/20 buffer/methanol. The activity was subsequently eluted from the column with 10 cuts (approximately 50 gallons each) of a solution of 50/50 buffer/methanol. The active cuts (approximately 1240 gmsA) were combined and diluted to a final concentration of 10% methanol by the addition of 1200 gallons of buffer. The use of dilution (rather than rotary evaporation) to reduce methanol concentration allowed the use of lower temperatures so as to minimize epi-hygromycin amounts, which tend to increase at higher temperatures. Half of this solution was loaded on a 40 liter CG-161 column (previously equilibrated with 4 bed volumes of a solution of 90/10 buffer/methanol). After loading, the column was washed with 4 bed volumes of 80/20 buffer/methanol and eluted with 5.5 bed volumes of 50/50 buffer/methanol. After regeneration and re-equilibration of the column, the second half of the activity was loaded on the column and eluted as described above. The combined cuts from both the runs (120 liters, approximately 1051 gmsA) were diluted to 10% methanol by the addition of buffer. This was re-loaded on the regenerated and re-equilibrated CG-161 resin column. Once the activity was adsorbed on the column, it was eluted with 4 bed volumes of methanol. This step served to both reduce the salts as well as increase the concentration of the sample prior to the final evaporation. The combined cuts from the final CG-161 column were evaporated to dryness to obtain a total of approximately 1 kgA of hygromycin A activity. The ratio of hygromycin A to epi-hygromycin in the final solids was about 14.5:1.

EXPERIMENTAL PROCEDURES FOR EXAMPLES

5″-Allyl Alcohol Preparations

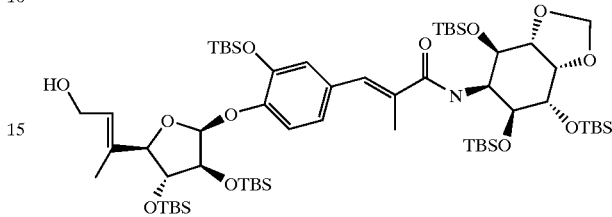

1. Preparation of E-Allyl Alcohol via Wittig Reaction

Method A

A solution of hygromycin A (1 eq.) and carboethoxymethylene triphenylphosphorane (2 eq.) in DMF (roughly 0.5 M in hygromycin) was allowed to stir at 70° C. for 5 hours and allowed to cool to room temperature. Imidazole (12 eq.) and tert-butyldimethylsilyl chloride (12 eq.) were added and the reaction was allowed to stir at 80° C. for 15 hours. The reaction was diluted with hexanes and diethyl ether (roughly 1:1), washed with water, then saturated sodium chloride solution, dried over magnesium sulfate, filtered and concentrated. The crude product was purified by silica gel chromatography, eluting with 10% ethyl acetate in hexanes.

A solution of the ethyl ester of hygromycin A (1 eq.) in methylene chloride (roughly 0.1M) at −78° C. was treated with diisobutyl aluminum hydride (4 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes.

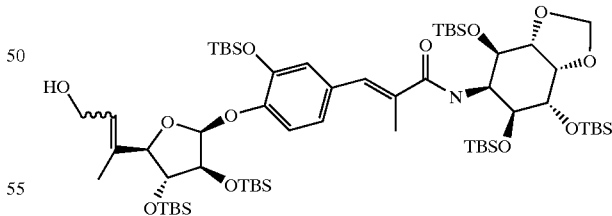

2. Preparation of E and Z-Allyl Alcohol via Peterson Reaction

Method B

A solution of hygromycin A (1 eq.), tert-butyldimethylsilyl chloride (12 eq.), and imidazole (12 eq.) in DMF (hygromycin concentration 0.25 M) was stirred at 80° C. for 20 hours. After removal of the DMF under reduced pressure, the resulting residue was extracted with diethyl ether. The combined ether extracts were washed with water, then saturated sodium chloride solution, dried over sodium sulfate, filtered, and concentrated. The crude product was purified by silica gel chromatography, eluting with 10% ethyl acetate in hexanes.

A solution of ethyl (trimethylsilyl)acetate (4 eq.) in THF (roughly 0.4 M in ethyl (trimethylsilyl)acetate) at −78° C. was treated with lithium diisopropylamide (3.5 eq.). After 30 minutes a solution of persilylated hygromycin A (1 eq.) in THF (roughly 0.5 M) was added. After 15 minutes the reaction was diluted with ethyl acetate and saturated ammonium chloride solution. The organic layer was washed with saturated ammonium chloride solution, then saturated sodium chloride solution, dried over magnesium sulfate, filtered and concentrated.

A solution of this crude ethyl ester (1 eq.) in methylene chloride (roughly 0.1M) at −78° C. was treated with diisobutyl aluminum hydride (8 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes to provide a mixture of E and Z allylic alcohols.

Method C

A solution of hygromycin A (1 eq.), tert-butyldimethylsilyl chloride (12 eq.), and imidazole (12 eq.) in DMF (hygromycin concentration 0.25 M) were stirred at 80° C. for 20 hours. After removal of the DMF under reduced pressure, the resulting residue was extracted with diethyl ether. The combined ether extracts were washed with water, then saturated sodium chloride solution, dried over sodium sulfate, filtered, and concentrated. The crude product was purified by silica gel chromatography, eluting with 10% ethyl acetate in hexanes.

A solution of methyl 2-(trimethylsilyl)propionate (5 eq.) in THF (roughly 0.2 M methyl 2-(trimethylsilyl)propionate) at −78° C. was treated with lithium diisopropylamide (4 eq.). After 30 minutes a solution of persilylated hygromycin A (1 eq.) in THF (roughly 0.4 M) was added. After 15 minutes the reaction was diluted with ethyl acetate and saturated ammonium chloride solution. The organic layer was washed with saturated ammonium chloride solution, then saturated sodium chloride solution, dried over magnesium sulfate, filtered and concentrated. A solution of this crude ethyl ester (1 eq.) in methylene chloride (roughly 0.1M) at −78° C. was treated with diisobutyl aluminum hydride (8 eq.). After treatment with saturated Rochelle's salt solution and warming to room temperature the reaction was diluted with methylene chloride, washed with saturated ammonium chloride solution, then saturated sodium chloride solution, dried over magnesium sulfate, filtered, and concentrated. The crude product was purified by silica gel chromatography, eluting with a step gradient of 5% ethyl acetate in hexanes to 33% ethyl acetate in hexanes to provide a mixture of E and Z allylic alcohols.

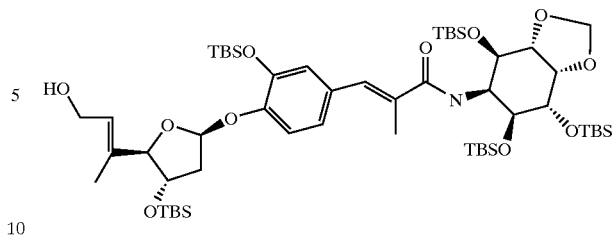

3. Preparation of 2″-Deoxy-E-Allyl Alcohol via Wittig Reaction

Method D

A solution of hygromycin A (1 eq.) in dimethylformamide (DMF, 0.1 M) was treated with imidazole (10 eq) and tert-butyidimethylsilyl chloride (10 eq) at 35° C. for 14–16 hours. The reaction was poured into water and extracted with ethyl acetate (EtOAc). The combined extracts were dried over MgSO4 and concentrated. The product was obtained after chromatography eluting with a step gradient of 5% ethyl acetate in hexanes to of 15% ethyl acetate in hexanes. A solution of the compound (1 eq.) in dichloroethane was treated with phenylthionochloroformate (3 eq.), pyridine (5 eq) and dimethylaminopyridine (0.05 eq.) at room temperature for 2–3 days. At the end of this time the reaction was diluted with methylene chloride, washed with 0.5 N HCl, saturated sodium bicarbonate and then brine. The organics were dried over $MgSO_4$ and concentrated. The desired 2″-thionocarbonate was obtained after chromatography, eluting with a step gradient of 5% ethyl acetate in hexanes to of 10% ethyl acetate in hexanes. A solution of the above 2″-thionocarbonate (1 eq.) in toluene (0.1 M) was treated with 2,2'-azobis(isobutyronitrile) (1 eq.) and tri-n-butyltinhydride (3 eq.) at 90° C. for 2 hours. The reaction was concentrated and chromatographed, eluting with a step gradient of 5% ethyl acetate in hexanes to of 10% ethyl acetate in hexanes, to provide the desired 2″-deoxy ketone.

A solution of penta-silyl protected hygromycin A (1 eq.) and carboethoxymethylene triphenylphosphorane (2 eq.) in DMF (roughly 0.5 M in hygromycin) was allowed to stir at 70° C. for 12 hours and allowed to cool to room temperature. Imidazole (1 eq.) and tert-butyldimethylsilyl chloride (1 eq.) were added and the reaction was allowed to stir at 70° C. for 4 hours. The reaction was diluted with hexanes and diethyl ether (roughly 1:1), washed with water, then saturated sodium chloride solution, dried over magnesium sulfate, filtered and concentrated. The crude product was purified by silica gel chromatography, eluting with a step gradient of 5% ethyl acetate in hexanes to 33% ethyl acetate in hexanes. A solution of the ethyl ester of hygromycin A (1 eq.) in methylene chloride (roughly 0.1M) at −78° C. was treated with diisobutyl aluminum hydride (4 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes.

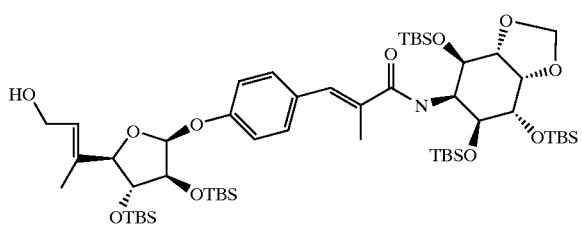

4. Preparation of 3-Deoxy-E-Allyl Alcohol via Wittig Reaction

Method E

Hygromycin A was treated with N-phenyl-bis(trifluoromethanesulphonamide) (1.8 eq.) and triethylamine (2 eq.) in DMF at room temperature for 2 h (hours). The solvent was removed en vacuo and the crude residue was chromatographed using a step gradient of 3% to 15% methanol in chloroform. A solution of the resultant phenyl triflate, tris(dibenzylidineacetone)dipalladium(0)-chloroform adduct (0.04 eq.), 1,1'-bis(diphenylphosphino)ferrocene (0.08 eq.) and triethylamine (7.5 eq.) in DMF was treated with formic acid (5 eq.) and warmed to 60° C. for 5 hours. The solvent was removed en vacuo and the crude residue was chromatographed using a step gradient of 3% to 20% methanol in chloroform to provide 3-deoxy hygromycin A as a mixture of epimers at C4".

3-deoxyhygromycin A was transformed into the desired 3-deoxy-E-allyl alcohol using method A described above.

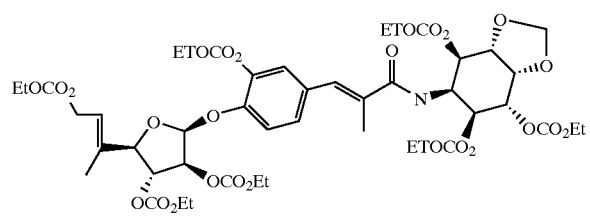

5. Preparation of Percarbonate Protected-E-Allyl Alcohol via Wittig Reaction Method F A solution of hygromycin A (1 eq.) and carboethoxymethylene triphenylphosphorane (2 eq.) in DMF (roughly 0.5 M in hygromycin) was allowed to stir at 70° C. for 5 hours and allowed to cool to room temperature. The solvent was removed under reduced pressure and the residue was purified by chromatography on silica, eluting with a step gradient of 3% methanol in chloroform to 15% methanol in chloroform to provide the desired unsaturated ester.

The above ester (1 eq) was dissolved in THF and cooled to −78° C. To this was slowly added a 1M solution of diisobutyl aluminum hydride (4 eq.) in $CH_2Cl_2$ over a period of ~0.5 h. After an additional 30 min the reaction was quenched by the addition of a saturated solution of Rochelle's salt and the mixture was allowed to warm to rt. The product was then adsorbed onto XAD-16 hydrophobic exchange resin (12 wt. eq) and the resin washed with water. The desired heptanol was obtained by washing the resin with methanol.

To a mixture of the above heptanol (1 eq.) and dimethylaminopyridine (20 eq.) was added of metyl pyrocarbonate (68 eq.) at 0° C. The mixture was warmed to room temperature and stirred for 30 min. The excess reagent was removed under reduced pressure, and purified by silica gel chromatography, eluting with 10% EtOAc in $CH_2Cl_2$ to give the desired heptacarbonate.

6. Preparation aldehydes such as: 5-chloro-2-fluoro-4-hydroxy-benzaldehyde

Method G

To 2-chloro-5-fluoro-phenol (1 eq.) in DMF (0.4 M) was added potassium carbonate (1.1 eq.) and methyl iodide (1.1 eq.). After 15 h the reaction was diluted with 1:1 hexanes:ethyl ether, washed with sat. ammonium chloride and brine, dried over magnesium sulfate, filtered and concentrated to afford pure anisole.

To 1-chloro-4-fluoro-2-methoxy-benzene (1 eq.) in methylene chloride (1 M) at 0° C. was slowly added a solution of titanium tetrachloride (1.6 eq.) in methylene chloride (1 M). To this was added a solution of dichloro-methoxy-methane (1.1 eq.) methylene chloride (0.1 M). The reaction was allowed to warm to room temperature. After 1 h the reaction was diluted with 1:1 hexanes:ethyl ether, washed with sat. sodium bicarbonate and brine, dried over sodium sulfate, filtered and concentrated. The product was obtained by chromatography on silica, eluting with a step gradient of 5% ethyl acetate in hexanes to 10% ethyl acetate in hexanes.

5-Chloro-2-fluoro-4-methoxy-benzaldehyde (1 eq.) and pyridine hydrochloride (5× by weight) were heated to 170° C. for 30 minutes. The reaction was cooled to room temperature and diluted with methylene chloride. The organic layer was washed with water and brine, dried over sodium sulfate, filtered and concentrated. The product was obtained by chromatography on silica, eluting with a step gradient of 10% acetone in hexanes to 33% acetone in hexanes.

(Aldehydes used in the below procedures made be prepared using the method above starting at the appropriate step with commercially available materials).

7. 5"-Allyl Derivative Preparations (Examples 1–328)

Method H (example 1: 3-(4-{(2S,3S,4S,5R)-5-[3-(4benzyaminomethyl-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;):

Silylated hygromycin allyl alcohol (1 eq.) in tetrahydrofuran (0.1 M) was treated with 3-chloro-4-hydroxy benzaldehyde (Florent et. Al. *J. Med Chem.* 1988, 3572) (1.1eq.), triphenylphosphine (1.2 eq.) and diethyl azodicarboxylate (1.2 eq). After completion (roughly 2 hours) the reaction was concentrated and chromatographed on silica (3–15% EtOAc/hexanes).

The persilated allyl ether was deprotected by treatment in THF (roughly 0.1M) with a solution of HF•pyridine/pyridine/THF for 30 to 45 hours at room temperature. The reaction was diluted with ethyl acetate, treated with solid $NaHCO_3$, filtered, concentrated and purified by silica gel chromatography, eluting with a step gradient of 5% methanol in methylene chloride to of 33% methanol in methylene chloride.

The above aldehyde (1 eq) and benxzyl amine (1.1 eg) in THF (0.05M) were treated with sodium triacetoxyborohydride (1.1 eg), and acetic acid (1.1 eg) at room temperature for 3 h. The reaction was concentrated and purified using a strong cation exchange resin with the product eluting with 3% amonium hydroxide in methanol. Alternatively, one skilled in the art can purify this compound and all of the compounds listed herein using reverse phase HPLC or preparative TLC as needed.

Method I (example 2: 3-(4-{(2S,3S,4S,5R)-5-[3-{2-chloro-4-[(methyl-napthalen-1-ylmethyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide):

The above aldehyde (1 eq) and N,N'-methyl-(napth-1-ylmethyl)-amine (1.1 eg) in DMF (0.07M) were treated with as (polystyrylmethyl)triemethylammonium cyanoborohydride (3 eg), and acetic acid (1.1 eg) at room temperature for 18 h. The reaction was concentrated and purified using a strong cation exchange resin with the product eluting with 3% ammonium hydroxide in methanol. Observed Mass Spec. 833.1, 835.2.

Method J (example 3: 3-(4-{(2S,3S,4S,5R)-5-[3-(2,3-Dichloro-4-{[(3-dimethylamino-propyl)-ethyl-amino]-methyl}-phenoxy)-1-methyl-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide)

Silylated hygromycin allyl alcohol (1 eq.) in toluene (0.1 M) was treated with 2,3-dichloro-4-hydroxy-benzaldehyde (method G) (1.5 eq.), triphenylphosphine (1.5 eq.) and diethyl azodicarboxylate (1.5 eq). After completion (roughly 1 h) the reaction was diluted with ethyl acetate, washed with pH 7 phosphate buffer (0.05 M) and brine. The organic layer was then dried over magnesium sulfate, filtered, concentrated and chromatographed on silica eluting with a step gradient of 5% ethyl acetate in hexanes to 50% ethyl acetate in hexanes.

The above aldehyde (1 eq), N-ethyl-N',N'-dimethyl-propane-1,3-diamine (1.3 eq.) and acetic acid (1.5 eq) in toluene (0.1 M) were treated with sodium triacetoxyborohydride (1.5 eq.) at 70° C. for 5 h. The reaction was cooled to room temperature and diluted with ethyl acetate. The organic layer was washed with water and brine, dried over sodium sulfate, filtered and concentrated and chromatographed on silica eluting with a step gradient of 10% methanol in methylene chloride to 20% methanol in methylene chloride.

The persilated allyl ether was deprotected by treatment in THF (roughly 0.1 M) with a solution of HF•pyridine/pyridine/THF for 14 hours at room temperature. The reaction was diluted with ethyl acetate and methanol (5:1), treated with solid NaHCO₃, filtered, concentrated and purified by silica gel chromatography, eluting with a step gradient of 10% methanol/1% ammonium hydroxide in methylene chloride to 30% methanol/3% ammonium hydroxide in methylene chloride.

Method K (Example 63. 3-(4-{(2S,3S,4S,5R)-5-[3-(2,3-Dichloro-4-{[(3-dimethylamino-2,2-dimethyl-propyl)-isobutyl-amino]-methyl}-phenoxy)-1-methyl-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide)

To protected aldehyde (method F) (1 eq.) in MeOH (0.1 M) was added N,N,2,2-tetramethyl-1,3-propanediamine (2 eq.). The reaction was heated to reflux for 15 h. After cooling to room temperature the reaction was diluted with dichloroethane (doubling volume) and sodium borohydride (3.7 eq.) was added (alternatively, sodium triacetoxyborohydride may be used). After 3 h the reaction was diluted with ethyl acetate, washed with pH 7 phosphate buffer (0.05 M) and brine. The organic layer was then dried over magnesium sulfate, filtered, concentrated and chromatographed on silica eluting with a step gradient of 2.5% methanol in methylene chloride to of 20% methanol in methylene chloride.

The above aldehyde (1 eq), isobutyraldehyde (2.2 eq.) and acetic acid (1 eq) in dichloroethane (0.1 M) were treated with sodium triacetoxyborohydride (2 eq.) at 60° C. for 16 h (in some cases an additional eq. of aldehyde and reductant needed to be added to drive the reaction to completion). The reaction was cooled to room temperature, diluted with methanol and allowed to stir for 1 h. After the solvents were evaporated the crude product was stirred in methanol and evaportated a second time. The desired product was obtained by chromatography on silica, eluting with a step gradient of 1% methanol in methylene chloride to 20% methanol in methylene chloride.

The persilated allyl ether was deprotected by treatment in THF (roughly 0.1 M) with a solution of HF•pyridine/pyridine/THF for 14 hours at room temperature. The reaction was diluted with ethyl acetate and methanol (5:1), treated with solid NaHCO₃, filtered, concentrated and purified by silica gel chromatography, eluting with a step gradient of 10% methanol/1% ammonium hydroxide in methylene chloride to of 30% methanol/3% ammonium hydroxide in methylene chloride.

Secondary amines may also be prepared by the above method by eliminating the second reductive amination step.

Method L (example 323) (3-(4-{(-{(2S,4S,5R)-5-[3-(4-{[Benzyl-(2-amino-ethyl)-amino]-methyl}-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide.

The above heptacarbonate (1 eq), phenol (2 eq), tetrakis (triphenylphosphine) palladium (0) (1.5 mole %), and KF-alumina (1.5 wt. eq) in THF (0.07 M) was stirred under argon at room temperature for 1.5 hrs. The reaction mixture was diluted with EtOAc and filtered through Celite. The residue obtained after evaporation of the solvents was purified by silica gel chromatography, eluting with a step gradient of 5% EtOAc in CH₂Cl₂ to 20% EtOAc in CH₂Cl₂) to give the desired phenyl allyl ether.

The phenol addition product (1 eq) was dissolved in 5:1 MeOH:hydrazine hydrate (0.03 M) at room temperature. The resulting solution was warmed to 60° C. for 4 hrs. The solvent and excess reagent were removed under reduced pressure, and the residue was purified by prep TLC, eluting with 30% MeOH in CH₂Cl₂ containing 0.4% NH₄OH to give example TABLE 1
5"-Allyl Derivatives
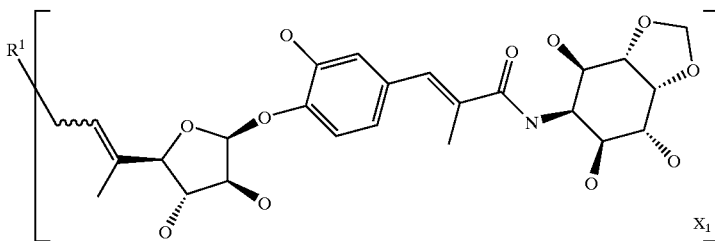
| Example | R1 | MW(Calc.) | MW(Obs) | E/Z | method |
|---|---|---|---|---|---|
| 1 | | 769.25 | 769.2 | E | H |
| 2 | | 833.34 | 833.8 | E | I |
| 3 | | 826.78 | 826.2 | E | J |
| 4 | | 830.381 | 830.2 | E | J |

TABLE 1-continued

5"-Allyl Derivatives

| Example | R1 | MW(Calc.) | MW(Obs) | E/Z | method |
|---------|----|-----------|---------|-----|--------|
| 5 | (2-chloro-4-oxy-benzyl)-N-[3-(4-methylpiperazin-1-yl)propyl]amine | 819.36 | 819.1 | E | J |
| 6 | (2-chloro-4-oxy-benzyl)-N-[2-(1-methylpyrrolidin-2-yl)ethyl]amine | 790.315 | 790.1 | E | J |
| 7 | (2-chloro-4-oxy-benzyl)-N-[2-(1-methylpyrrol-2-yl)ethyl]amine | 786.283 | 786.1 | E | J |
| 8 | (2-chloro-4-oxy-benzyl)-N-methyl-N-(1-methylpyrrolidin-3-yl)amine | 776.288 | 776.2 | E | J |
| 9 | valinamide-N-(2,3-dichloro-4-oxy-benzyl) derivative | 812.705 | 812.2 | E | J |

TABLE 1-continued

5"-Allyl Derivatives

| Example | R1 | MW(Calc.) | MW(Obs) | E/Z | method |
|---|---|---|---|---|---|
| 10 | (dimethylaminopropyl-ethylamino-methyl-chlorophenoxy) | 792.33 | 792.3 | E | I |
| 11 | (indolyl-ethylamino-methyl-dichlorophenoxy) | 856.76 | 856.2 | E | K |
| 12 | (isopentylamino-methyl-dichlorophenoxy) | 783.71 | 784.7 | E | K |
| 13 | (indanyl-amino-methyl-dichlorophenoxy) | 829.74 | 829.4 | E | K |
| 14 | (propylamino-methyl-dichlorophenoxy) | 755.65 | 756.8 | E | K |

TABLE 1-continued
5"-Allyl Derivatives
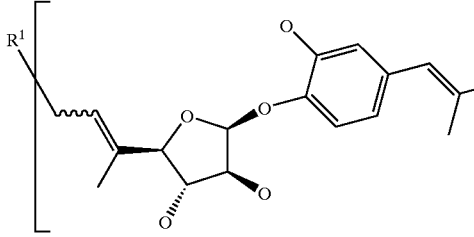
| Example | R1 | MW(Calc.) | MW(Obs) | E/Z | method |
|---|---|---|---|---|---|
| 15 | 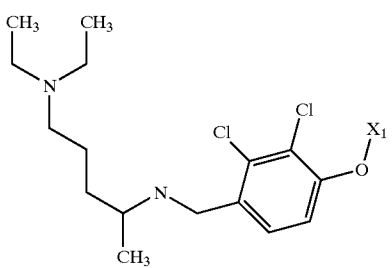 | 886.83 | 887.8 | E | K |
| 16 | 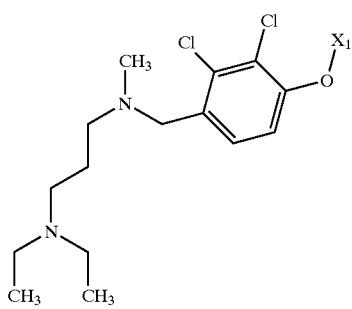 | 854.83 | 855.8 | E | K |
| 17 | 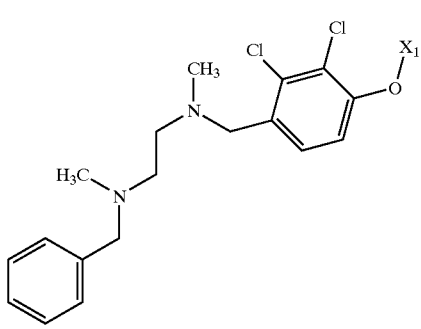 | 840.80 | 840.5 | E | J |
| 18 |  | 874.82 | 875.8 | E | J |

TABLE 1-continued

5"-Allyl Derivatives

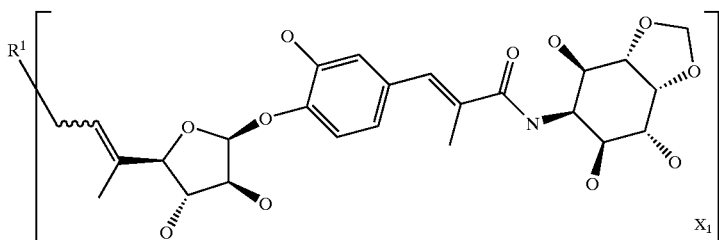

| Example | R1 | MW(Calc.) | MW(Obs) | E/Z | method |
|---|---|---|---|---|---|
| 19 | (N,N-dimethylaminoethyl)(benzyl)aminomethyl-2,3-dichlorophenoxy | 874.82 | 875.8 | E | J |
| 20 | (dimethylamino)methyl-2,3-dichlorophenoxy | 741.63 | 743.4 | E | J |
| 21 | (cyclopropylmethyl)(propyl)aminomethyl-2,3-dichlorophenoxy | 809.75 | 810.9 | E | J |
| 22 | (diethylamino)methyl-2,3-dichlorophenoxy | 769.68 | missing | E | J |
| 23 | [3-(4-methylpiperazin-1-yl)propyl](ethyl)aminomethyl-2,3-dichlorophenoxy | 881.86 | 882.9 | E | J |
| 24 | [4-(piperidin-1-yl)butyl](methyl)aminomethyl-2,3-dichlorophenoxy | 866.84 | 867.9 | E | J |

TABLE 1-continued
5"-Allyl Derivatives
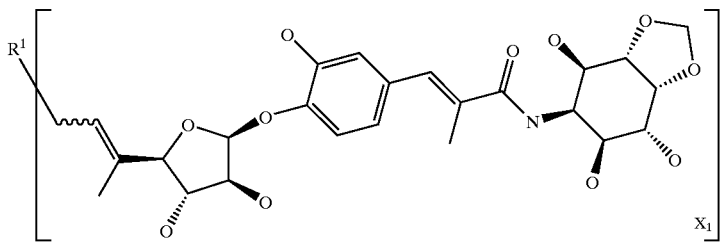
| Example | R1 | MW(Calc.) | MW(Obs) | E/Z | method |
|---|---|---|---|---|---|
| 25 | (2,3-dichloro-4-oxy-benzyl)-N-methyl-N-(3-dimethylaminopropyl) | 812.75 | 813.9 | E | J |
| 26 | (2-fluoro-5-chloro-4-oxy-benzyl)-N-(2-(indol-3-yl)ethyl) | 840.31 | 838.2 | E | K |
| 27 | (2-fluoro-5-chloro-4-oxy-benzyl)-N-cycloheptyl | 793.29 | 793.6 | E | K |
| 28 | (2-fluoro-5-chloro-4-oxy-benzyl)-N-isopentyl | 767.25 | 767.5 | E | K |
| 29 | (2-fluoro-5-chloro-4-oxy-benzyl)-N-(indan-1-yl) | 813.28 | 813.3 | E | K |
| 30 | (2-fluoro-5-chloro-4-oxy-benzyl)-N-(1-benzylpiperidin-4-yl) | 870.38 | 870.3 | E | K |

TABLE 1-continued
5"-Allyl Derivatives
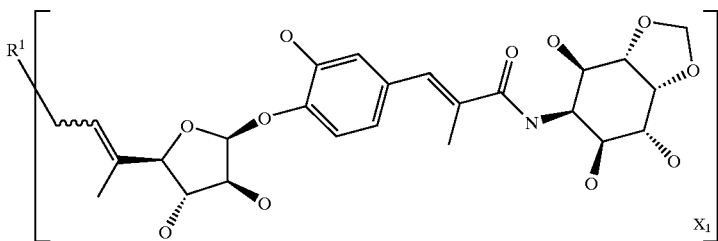
| Example | R1 | MW(Calc.) | MW(Obs) | E/Z | method |
|---|---|---|---|---|---|
| 31 | (2-F, 5-Cl, 4-OX₁-benzyl)(cyclopropylmethyl)amine | 751.21 | 751.2 | E | K |
| 32 | N,N-diethyl-N'-(2-F, 5-Cl, 4-OX₁-benzyl)-pentane-1,4-diamine | 838.38 | 838.7 | E | K |
| 33 | N-(2-F, 5-Cl, 4-OX₁-benzyl)-N-methyl-N',N'-diethyl-propane-1,3-diamine | 824.35 | 824.7 | E | J |
| 34 | N-benzyl-N-methyl-N'-(2-F, 5-Cl, 4-OX₁-benzyl)-N'-methyl-ethane-1,2-diamine | 858.37 | 858.6 | E | J |
| 35 | N-benzyl-N-(2-F, 5-Cl, 4-OX₁-benzyl)-N',N'-dimethyl-ethane-1,2-diamine | 858.37 | 858.3 | E | J |

TABLE 1-continued

5"-Allyl Derivatives

| Example | R1 | MW(Calc.) | MW(Obs) | E/Z | method |
|---|---|---|---|---|---|
| 36 | | 725.17 | 725.5 | E | J |
| 37 | | 793.29 | 793.3 | E | J |
| 38 | | 865.40 | 865.3 | E | J |
| 39 | | 850.39 | 850.7 | E | J |
| 40 | | 816.28 | 816.3 | E | J |
| 41 | | 782.27 | 782.3 | E | J |

TABLE 1-continued
5"-Allyl Derivatives
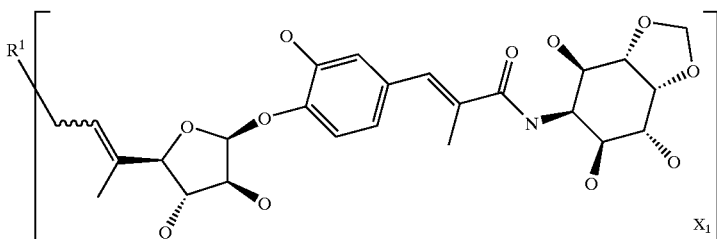
| Example | R1 | MW(Calc.) | MW(Obs) | E/Z | method |
|---|---|---|---|---|---|
| 42 | (4-dimethylaminopropyl-methylamino-methyl)-2-fluoro-5-chlorophenyl | 796.29 | 796.6 | E | J |
| 43 | (2-(indol-3-yl)ethyl-amino-methyl)-2-chlorophenyl | 822.32 | 820.3 | E | K |
| 44 | (cycloheptylamino-methyl)-2-chlorophenyl | 775.30 | 775.3 | E | K |
| 45 | (isopentylamino-methyl)-2-chlorophenyl | 749.26 | 749.3 | E | K |
| 46 | (indan-1-yl-amino-methyl)-2-chlorophenyl | 795.29 | 795.6 | E | K |
| 47 | (propylamino-methyl)-2-chlorophenyl | 721.21 | 721.3 | E | K |

TABLE 1-continued
5"-Allyl Derivatives
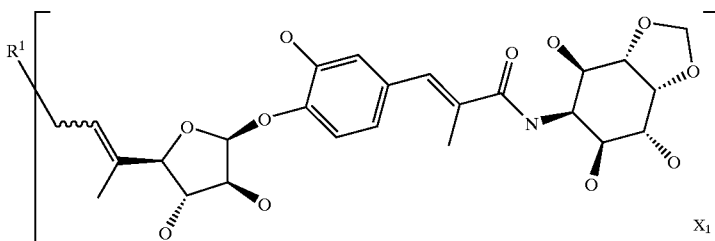
| Example | R1 | MW(Calc.) | MW(Obs) | E/Z | method |
|---|---|---|---|---|---|
| 48 | *1-benzylpiperidin-4-yl-amino, 2-Cl-4-O-X₁ benzyl* | 852.39 | 852.3 | E | K |
| 49 | *cyclopropylmethylamino, 2-Cl-4-O-X₁ benzyl* | 733.22 | 733.5 | E | K |
| 50 | *4-(diethylamino)pentan-2-yl-amino, 2-Cl-4-O-X₁ benzyl* | 820.39 | 820.3 | E | K |
| 51 | *3-(diethylamino)propyl-N-methyl-amino, 2-Cl-4-O-X₁ benzyl* | 806.36 | 806.3 | E | J |
| 52 | *2-(N-benzyl-N-methylamino)ethyl-N-methyl-amino, 2-Cl-4-O-X₁ benzyl* | 840.38 | 840.3 | E | J |

TABLE 1-continued

5"-Allyl Derivatives

| Example | R1 | MW(Calc.) | MW(Obs) | E/Z | method |
|---------|----|-----------|---------|-----|--------|
| 53 | (benzyl)(2-(dimethylamino)ethyl)aminomethyl-2-chloro-4-O-phenyl | 840.38 | 840.6 | E | J |
| 54 | (dimethylamino)methyl-2-chloro-4-O-phenyl | 707.18 | 707.2 | E | J |
| 55 | (cyclopropylmethyl)(propyl)aminomethyl-2-chloro-4-O-phenyl | 775.30 | 775.6 | E | J |
| 56 | (3-(4-methylpiperazin-1-yl)propyl)(ethyl)aminomethyl-2-chloro-4-O-phenyl | 847.41 | 847.7 | E | J |
| 57 | (4-(piperidin-1-yl)butyl)(methyl)aminomethyl-2-chloro-4-O-phenyl | 832.40 | 832.7 | E | J |
| 58 | (2-(pyridin-4-yl)ethyl)(methyl)aminomethyl-2-chloro-4-O-phenyl | 798.29 | 798.3 | E | J |
| 59 | (2-(dimethylamino)ethyl)(methyl)aminomethyl-2-chloro-4-O-phenyl | 764.28 | 764.3 | E | J |

TABLE 1-continued

5"-Allyl Derivatives

| Example | R1 | MW(Calc.) | MW(Obs) | E/Z | method |
|---------|----|-----------|---------|-----|--------|
| 60 | | 778.30 | 778.3 | E | J |
| 61 | | 810.73 | 810.3 | E | J |
| 62 | | 886.83 | 886.0 | E | J |
| 63 | | 882.89 | 882.3 | E | K |
| 64 | | 809.75 | 809.3 | E | K |

TABLE 1-continued

5"-Allyl Derivatives

| Example | R1 | MW(Calc.) | MW(Obs) | E/Z | method |
|---|---|---|---|---|---|
| 65 | (2-hydroxyethyl)(propyl)aminomethyl-2,3-dichlorophenyl ether | 799.71 | 799.2 | E | J |
| 66 | (methyl)(2-(pyridin-4-yl)ethyl)aminomethyl-2,3-dichlorophenyl ether | 832.74 | 832.1 | E | J |
| 67 | (methyl)(2-(dimethylamino)ethyl)aminomethyl-2,3-dichlorophenyl ether | 798.72 | 798.2 | E | J |
| 68 | (propyl)aminomethyl-5-chloro-2-fluorophenyl ether | 739.20 | 739.3 | E | K |
| 69 | (2-hydroxyethyl)(propyl)aminomethyl-5-chloro-2-fluorophenyl ether | 783.25 | 783.3 | E | J |

TABLE 1-continued
5''-Allyl Derivatives
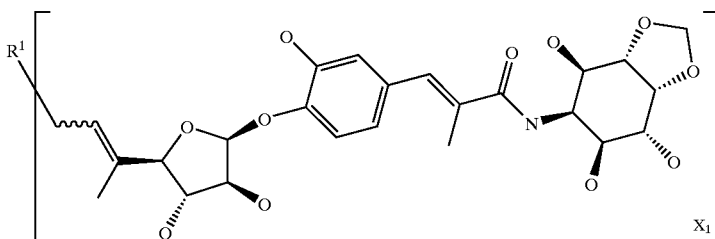
| Example | R1 | MW(Calc.) | MW(Obs) | E/Z | method |
|---|---|---|---|---|---|
| 70 | | 765.26 | 765.3 | E | J |
| 71 | | 916.90 | 916.2 | E | K |
| 72 | | 942.94 | 942.3 | E | K |
| 73 | | 932.90 | 933.9 | E | K |
| 74 | | 898.88 | 898.1 | E | K |

TABLE 1-continued
5''-Allyl Derivatives
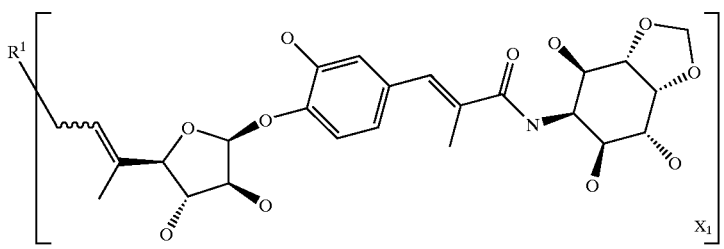
| Example | R1 | MW(Calc.) | MW(Obs) | E/Z | method |
|---|---|---|---|---|---|
| 75 | | 800.65 | 799.8 | E | K |
| 76 | | 826.73 | 825.6 | E | K |
| 77 | | 796.71 | 840.0 | E | J |
| 78 | | 810.69 | 809.8 | E | J |
| 79 | | 890.78 | 889.7 | E | K |

TABLE 1-continued
5"-Allyl Derivatives
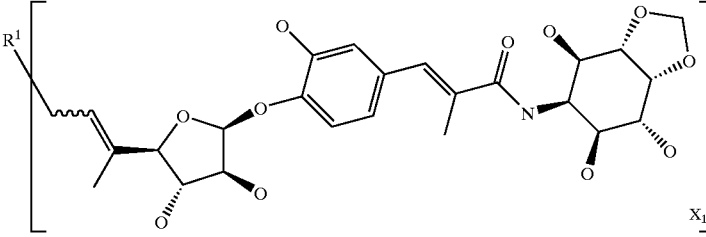
| Example | R1 | MW(Calc.) | MW(Obs) | E/Z | method |
|---|---|---|---|---|---|
| 80 | 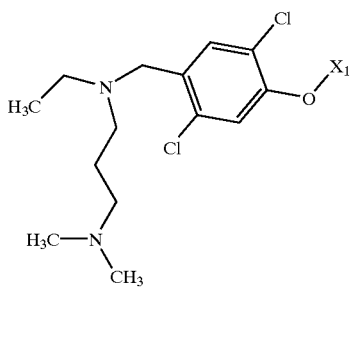 | 826.78 | 826.3 | E | I |
| 81 | 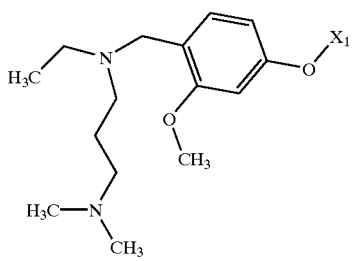 | 810.32 | 810.4 | E | I |
| 82 | 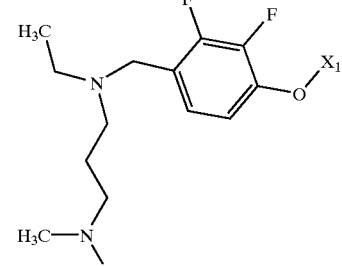 | 787.91 | 788.3 | E | J |
| 83 | | 793.87 | 794.3 | E | J |

TABLE 1-continued
5"-Allyl Derivatives
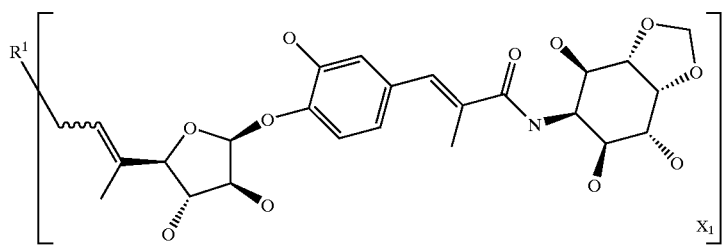
| Example | R1 | MW(Calc.) | MW(Obs) | E/Z | method |
|---|---|---|---|---|---|
| 84 | (ethyl)(3-(dimethylamino)propyl)aminomethyl-3-fluoro-phenoxy | 775.88 | 776.5 | E | J |
| 85 | (ethyl)(3-(dimethylamino)propyl)aminomethyl-2-fluoro-phenoxy | 775.88 | 776.5 | E | J |
| 86 | (4-methylpiperazin-1-yl)methyl-2,3-dichloro-phenoxy | 796.71 | 796.3 | E | J |
| 87 | (4-benzylpiperazin-1-yl)methyl-2,3-dichloro-phenoxy | 872.81 | 872.4 | E | J |
| 88 | (4-(pyridin-2-yl)piperazin-1-yl)methyl-2,3-dichloro-phenoxy | 859.77 | 859.4 | E | J |

TABLE 1-continued

5"-Allyl Derivatives

| Example | R1 | MW(Calc.) | MW(Obs) | E/Z | method |
|---------|----|-----------|---------|-----|--------|
| 89 | | 866.84 | 866.2 | E | I |
| 90 | | 882.89 | 882.3 | E | I |
| 91 | | 868.86 | 868.2 | E | I |
| 92 | | 902.88 | 902.1 | E | I |

TABLE 1-continued
5"-Allyl Derivatives
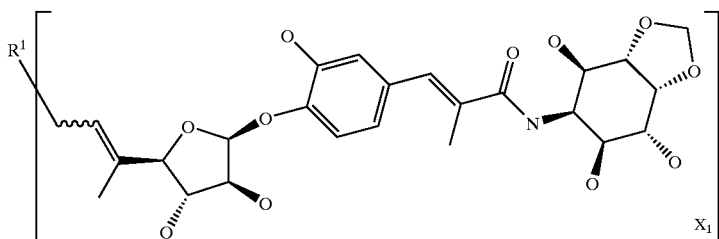
| Example | R1 | MW(Calc.) | MW(Obs) | E/Z | method |
|---|---|---|---|---|---|
| 93 | (diethylaminopropyl)(cyclopropylmethyl)amino-2,3-dichlorobenzyl-O-X₁ | 880.87 | 880.1 | E | I |
| 94 | (diethylaminopropyl)(isopentyl)amino-2,3-dichlorobenzyl-O-X₁ | 896.91 | 896.2 | E | I |
| 95 | (diethylaminopropyl)(isobutyl)amino-2,3-dichlorobenzyl-O-X₁ | 882.89 | 882.2 | E | I |
| 96 | (diethylaminopropyl)(benzyl)amino-2,3-dichlorobenzyl-O-X₁ | 916.90 | 916.1 | E | I |

TABLE 1-continued
5"-Allyl Derivatives
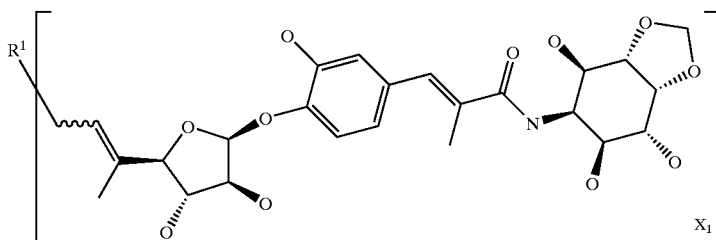
| Example | R1 | MW(Calc.) | MW(Obs) | E/Z | method |
|---|---|---|---|---|---|
| 97 | | 840.80 | 840.2 | E | J |
| 98 | | 854.83 | 853.9 | E | I |
| 99 | | 841.79 | 841.1 | E | I |
| 100 | | 869.84 | 869.1 | E | I |

TABLE 1-continued
5"-Allyl Derivatives
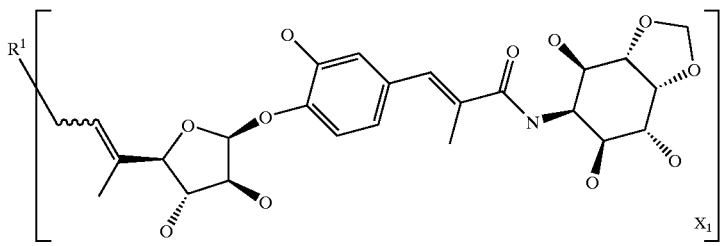
| Example | R1 | MW(Calc.) | MW(Obs) | E/Z | method |
|---|---|---|---|---|---|
| 101 | (N-methyl-N-[1-methyl-2-(4-chlorophenyl)ethyl]aminomethyl)-3-chloro-4-O-X₁-phenyl | 845.78 | 846.1 | E | I |
| 102 | (N-propyl-N-cyclopropylmethylaminomethyl)-3-chloro-4-O-X₁-phenyl | 775.3 | 775.5 | E | I |
| 103 | (N-methyl-N-(2-hydroxyethyl)aminomethyl)-3-chloro-4-O-X₁-phenyl | 737.21 | 737.5 | E | I |
| 104 | (N,N-dimethylaminomethyl)-3-chloro-4-O-X₁-phenyl | 707.18 | 707.5 | E | I |

TABLE 1-continued
5''-Allyl Derivatives
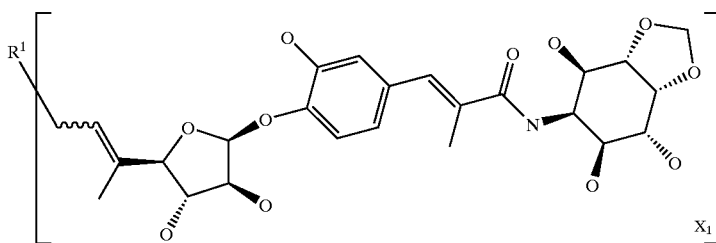
| Example | R1 | MW(Calc.) | MW(Obs) | E/Z | method |
|---|---|---|---|---|---|
| 105 | | 765.26 | 765.5 | E | I |
| 106 | | 749.26 | 749.6 | E | I |
| 107 | | 751.19 | 751.5 | E | I |

TABLE 1-continued
5"-Allyl Derivatives
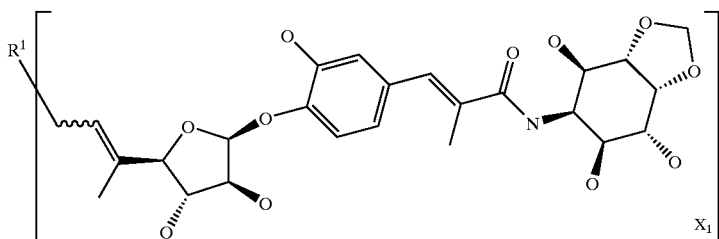
| Example | R1 | MW(Calc.) | MW(Obs) | E/Z | method |
|---------|----|-----------|---------|-----|--------|
| 108 | 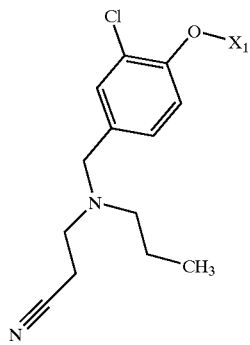 | 774.27 | 774.6 | E | I |
| 109 | 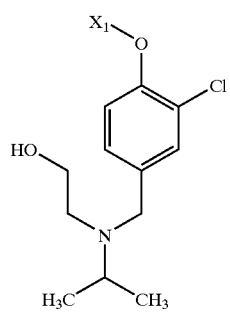 | 765.26 | 765.6 | E | I |
| 110 | 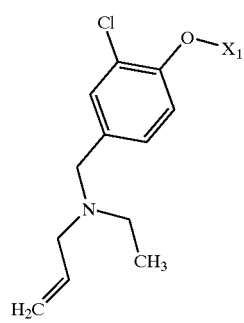 | 747.25 | 747.6 | E | I |

TABLE 1-continued

5"-Allyl Derivatives

| Example | R1 | MW(Calc.) | MW(Obs) | E/Z | method |
|---|---|---|---|---|---|
| 111 | (3-chloro-4-oxy-benzyl)-N-methyl-N-(2-methylallyl)amine | 747.25 | 747.7 | E | I |
| 112 | (3-chloro-4-oxy-benzyl)-N-isopropyl-N-(2-methoxyethyl)amine | 779.29 | 779.7 | E | I |
| 113 | (3-chloro-4-oxy-benzyl)-N-ethyl-N-(2-methoxyethyl)amine | 765.26 | 765.7 | E | I |

TABLE 1-continued
5"-Allyl Derivatives
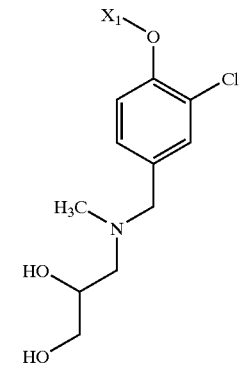
| Example | R1 | MW(Calc.) | MW(Obs) | E/Z | method |
|---|---|---|---|---|---|
| 114 | 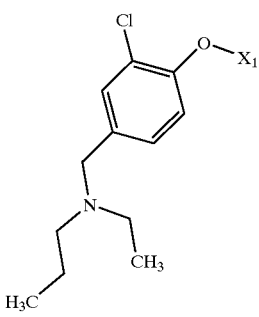 | 767.23 | 767.7 | E | I |
| 115 | | 749.26 | 749.7 | E | I |
| 116 | 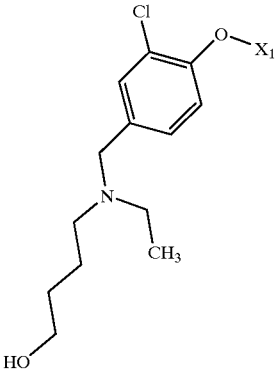 | 779.29 | 779.8 | E | I |

TABLE 1-continued
5"-Allyl Derivatives
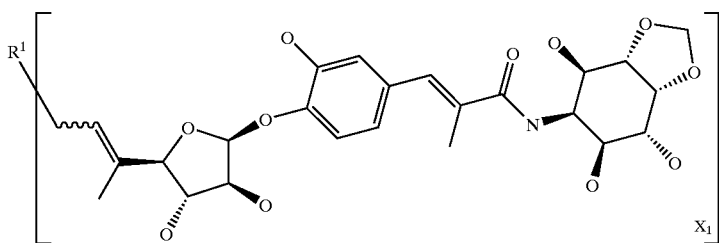
| Example | R1 | MW(Calc.) | MW(Obs) | E/Z | method |
|---|---|---|---|---|---|
| 117 | | 751.24 | 751.7 | E | I |
| 118 | | 749.26 | 749.8 | E | I |
| 119 | | 721.21 | 721.6 | E | I |

TABLE 1-continued
5"-Allyl Derivatives
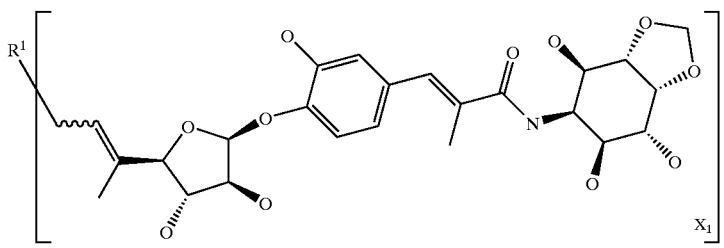
| Example | R1 | MW(Calc.) | MW(Obs) | E/Z | method |
|---|---|---|---|---|---|
| 120 | 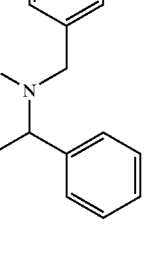 | 859.38 | 859.8 | E | I |
| 121 | 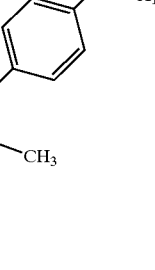 | 733.22 | 733.7 | E | I |
| 122 | 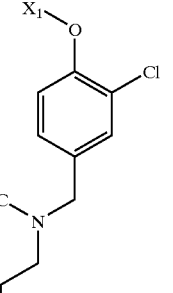 | 764.28 | 765.1 | E | I |

TABLE 1-continued
5"-Allyl Derivatives
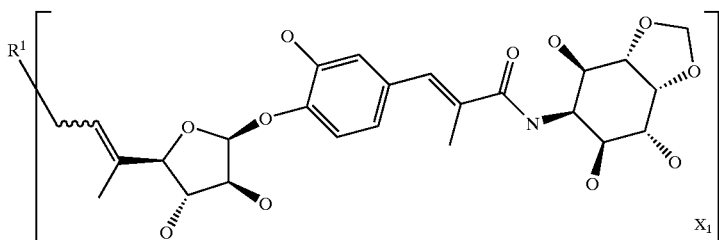
| Example | R1 | MW(Calc.) | MW(Obs) | E/Z | method |
|---|---|---|---|---|---|
| 123 | | 773.24 | 773.7 | E | I |
| 124 | | 778.3 | 779.1 | E | I |
| 125 | | 763.29 | 763.8 | E | I |

TABLE 1-continued
5"-Allyl Derivatives
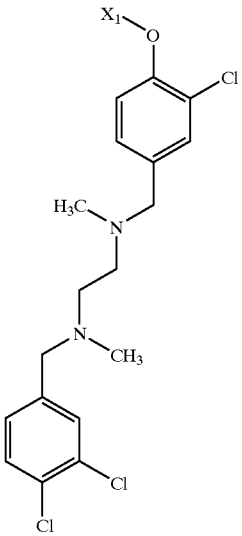
| Example | R1 | MW(Calc.) | MW(Obs) | E/Z | method |
|---|---|---|---|---|---|
| 126 | 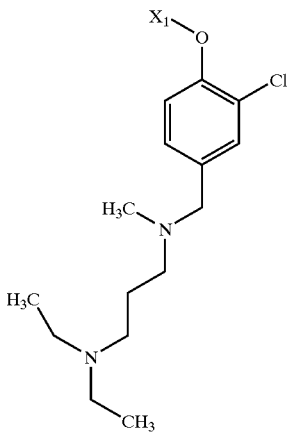 | 909.27 | 910.5 | E | I |
| 127 | | 806.36 | 807.2 | E | I |

TABLE 1-continued
5"-Allyl Derivatives
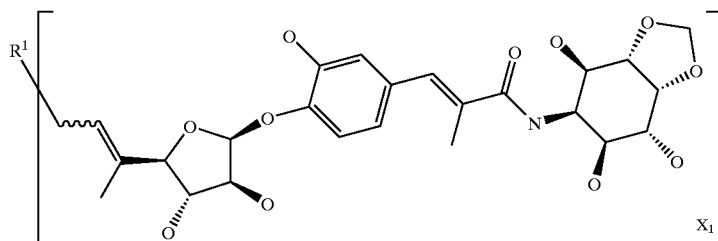
| Example | R1 | MW(Calc.) | MW(Obs) | E/Z | method |
|---|---|---|---|---|---|
| 128 | | 840.38 | 840.9 | E | I |
| 129 | | 827.33 | 827.8 | E | I |
| 130 | | 839.34 | 842.2 | E | I |

TABLE 1-continued
5''-Allyl Derivatives
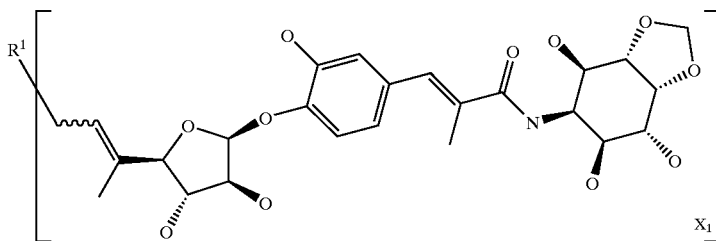
| Example | R1 | MW(Calc.) | MW(Obs) | E/Z | method |
|---|---|---|---|---|---|
| 131 | (3-chloro-4-oxy-benzyl)(2-cyanoethyl)(pyridin-3-ylmethyl)amine | 823.3 | 823.8 | E | I |
| 132 | (3-chloro-4-oxy-benzyl)(isopropyl)(2-hydroxy-2-(3,4-dihydroxyphenyl)ethyl)amine | 873.36 | 873.8 | E | I |
| 133 | (3-chloro-4-oxy-benzyl)(benzyl)(2-phenylethyl)amine | 873.41 | 873.9 | E | I |

TABLE 1-continued
5"-Allyl Derivatives
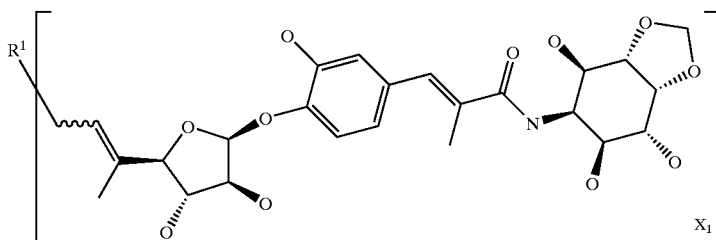
| Example | R1 | MW(Calc.) | MW(Obs) | E/Z | method |
|---|---|---|---|---|---|
| 134 | (3-chloro-4-substituted-benzyl)(N-methyl)(1-methyl-2-(2-methoxyphenyl)ethyl)amine | 841.36 | 842.2 | E | I |
| 135 | (3-chloro-4-substituted-benzyl)(N-methyl)(2-hydroxy-2-phenylethyl)amine | 813.31 | 813.8 | E | I |
| 136 | (3-chloro-4-substituted-benzyl)(diisobutyl)amine | 791.34 | 791.9 | E | I |

TABLE 1-continued
5"-Allyl Derivatives
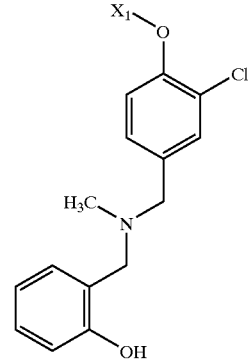
| Example | R1 | MW(Calc.) | MW(Obs) | E/Z | method |
|---|---|---|---|---|---|
| 137 | 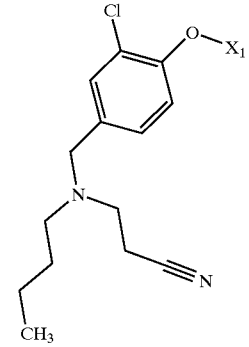 | 799.28 | 799.8 | E | I |
| 138 | 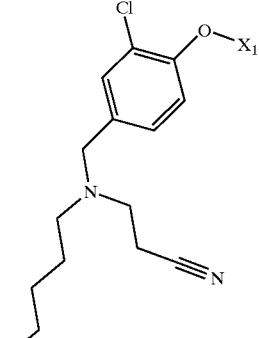 | 788.3 | 788.8 | E | I |
| 139 | | 816.35 | 816.9 | E | I |

TABLE 1-continued
5"-Allyl Derivatives
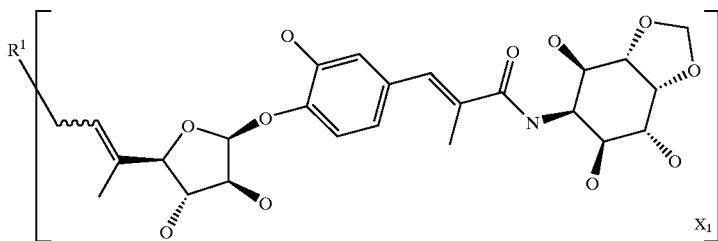
| Example | R1 | MW(Calc.) | MW(Obs) | E/Z | method |
|---|---|---|---|---|---|
| 140 | | 858.44 | 858.9 | E | I |
| 141 | | 812.32 | 812.8 | E | I |
| 142 | | 816.31 | 816.8 | E | I |

TABLE 1-continued
5"-Allyl Derivatives
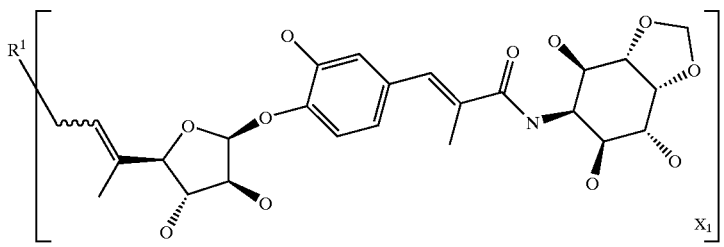
| Example | R1 | MW(Calc.) | MW(Obs) | E/Z | method |
|---|---|---|---|---|---|
| 143 | | 807.34 | 808.2 | E | I |
| 144 | | 841.36 | 841.9 | E | I |
| 145 | | 841.36 | 841.9 | E | I |

TABLE 1-continued
5"-Allyl Derivatives
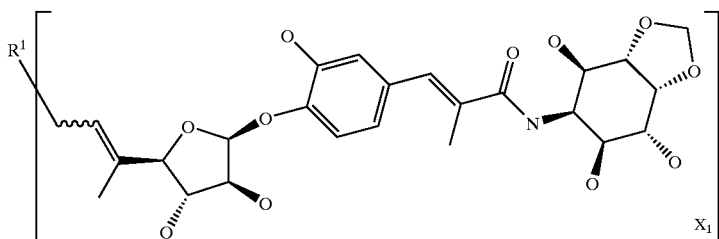
| Example | R1 | MW(Calc.) | MW(Obs) | E/Z | method |
|---|---|---|---|---|---|
| 146 | 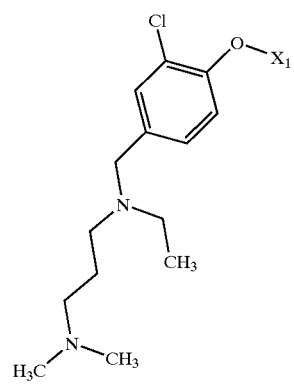 | 792.33 | 793.2 | E | I |
| 147 | 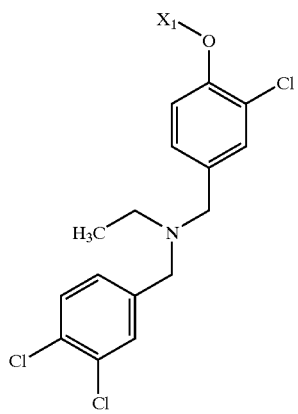 | 866.2 | 867.5 | E | I |
| 148 | 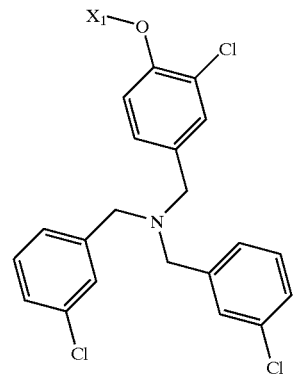 | 928.27 | 928.2 | E | I |

TABLE 1-continued
5"-Allyl Derivatives
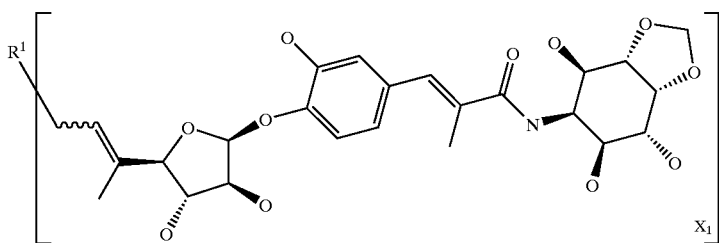
| Example | R1 | MW(Calc.) | MW(Obs) | E/Z | method |
|---|---|---|---|---|---|
| 149 | | 889.41 | 891.4 | E | I |
| 150 | | 839.39 | 840.2 | E | I |
| 151 | | 845.78 | 846.2 | E | I |

TABLE 1-continued
5"-Allyl Derivatives
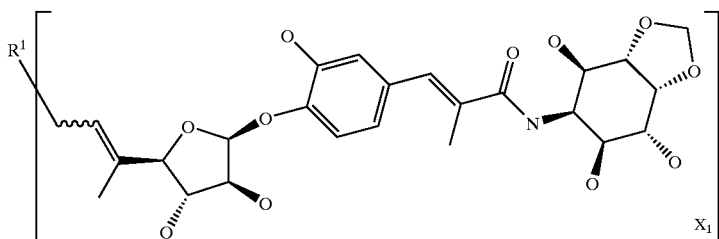
| Example | R1 | MW(Calc.) | MW(Obs) | E/Z | method |
|---|---|---|---|---|---|
| 152 | 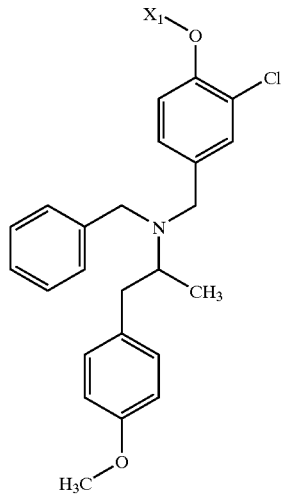 | 917.46 | 919.5 | E | I |
| 153 | 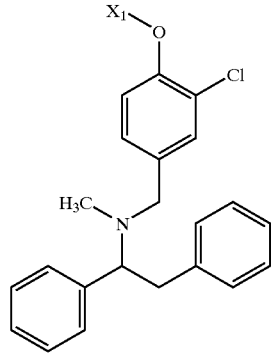 | 873.41 | 847.3 | E | I |

TABLE 1-continued
5"-Allyl Derivatives
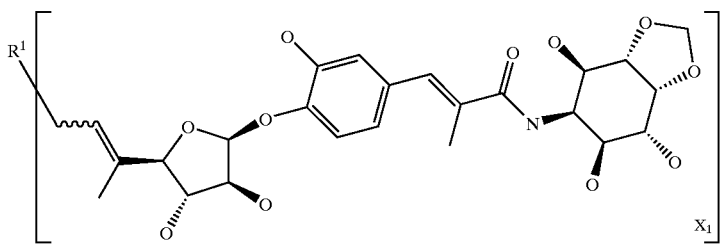
| Example | R1 | MW(Calc.) | MW(Obs) | E/Z | method |
|---|---|---|---|---|---|
| 154 | 3-Cl, 4-(O-X$_1$)-benzyl-N-methyl-N-octyl | 805.37 | 805.9 | E | I |
| 155 | 3-Cl, 4-(O-X$_1$)-benzyl-N-methyl-N-(4-methylbenzyl) | 811.33 | 811.9 | E | I |
| 156 | 3-Cl, 4-(O-X$_1$)-benzyl-N,N-dipentyl | 819.4 | 819.9 | E | I |

TABLE 1-continued
5"-Allyl Derivatives
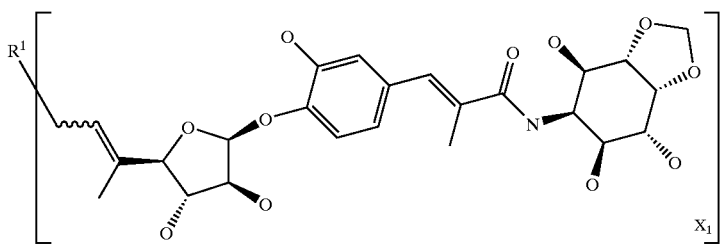
| Example | R1 | MW(Calc.) | MW(Obs) | E/Z | method |
|---|---|---|---|---|---|
| 157 | 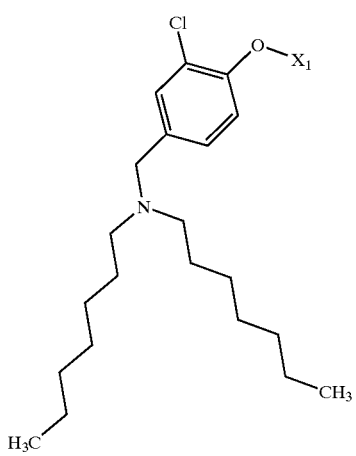 | 875.51 | 876 | E | I |
| 158 | 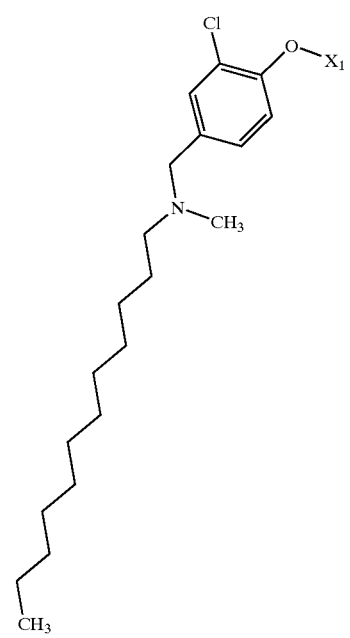 | 861.48 | 862 | E | I |

TABLE 1-continued
5"-Allyl Derivatives
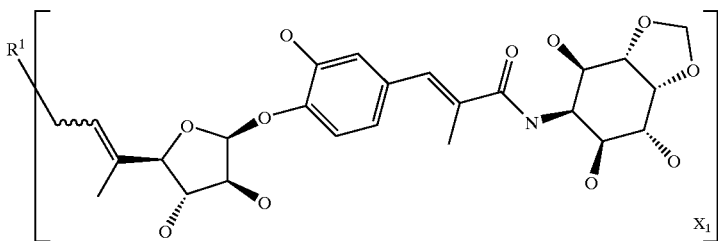
| Example | R1 | MW(Calc.) | MW(Obs) | E/Z | method |
|---|---|---|---|---|---|
| 159 | ![R1 structure: X1-O-phenyl(Cl)-CH2-N(CH3)-CH2-phenyl] | 783.28 | 783.8 | E | I |
| 160 | ![R1 structure: X1-O-phenyl(Cl)-CH2-N(CH3)-CH2CH2-(2-pyridyl)] | 798.29 | 799.1 | E | I |
| 161 | ![R1 structure: X1-O-phenyl(Cl)-CH2-N(CH3)-CH2CH2-(4-pyridyl)] | 798.29 | 799.2 | E | I |

TABLE 1-continued
5"-Allyl Derivatives
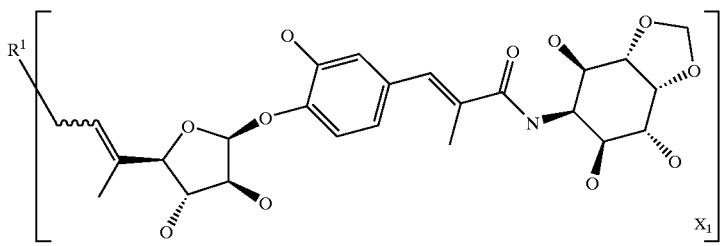
| Example | R1 | MW(Calc.) | MW(Obs) | E/Z | method |
|---|---|---|---|---|---|
| 162 | (3-chloro-4-oxyphenyl)methyl-N-methyl-N-[2-(3,4-dimethoxyphenyl)ethyl]amine | 857.36 | 857.9 | E | I |
| 163 | (3-chloro-4-oxyphenyl)methyl-N-ethyl-N-(pyridin-4-ylmethyl)amine | 798.29 | 798.8 | E | I |
| 164 | (3-chloro-4-oxyphenyl)methyl-N-methyl-N-(2-phenylethyl)amine | 797.31 | 797.8 | E | I |

TABLE 1-continued
5"-Allyl Derivatives
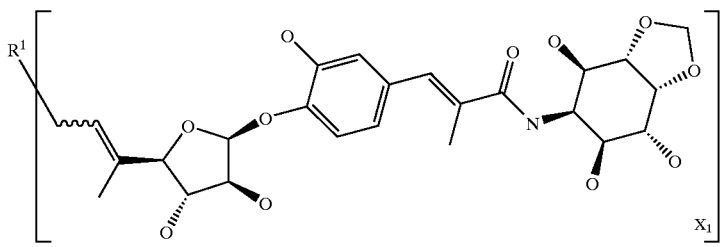
| Example | R1 | MW(Calc.) | MW(Obs) | E/Z | method |
|---|---|---|---|---|---|
| 165 | | 825.36 | 825.8 | E | I |
| 166 | | 817.73 | 819.4 | E | I |
| 167 | | 827.33 | 827.8 | E | I |

TABLE 1-continued
5"-Allyl Derivatives
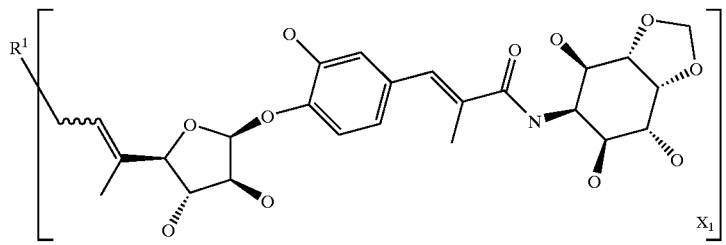
| Example | R1 | MW(Calc.) | MW(Obs) | E/Z | method |
|---|---|---|---|---|---|
| 168 | (3-chloro-4-(X₁-O)benzyl)-N-methyl-N-(2-(N-benzyl-N-methylamino)ethyl)amine | 840.38 | 840.9 | E | I |
| 169 | (3-chloro-4-(X₁-O)benzyl)-N-methyl-N-((R)-1-phenylethyl)amine | 797.31 | 797.8 | E | I |
| 170 | (3-chloro-4-(X₁-O)benzyl)-N-methyl-N-((1R,2S)-1-hydroxy-1-phenylprop-2-yl)amine | 827.33 | 827.9 | E | I |

TABLE 1-continued

5"-Allyl Derivatives

| Example | R1 | MW(Calc.) | MW(Obs) | E/Z | method |
|---|---|---|---|---|---|
| 171 | (3-chloro-4-oxy-benzyl)-N-methyl-N-phenylalanine substituent | 841.32 | 841.8 | E | I |
| 172 | (3-chloro-4-oxy-benzyl)-N-methyl-N-[2-(3,4-dihydroxyphenyl)ethyl]amine substituent | 829.31 | 829.8 | E | I |
| 173 | (3-chloro-4-oxy-benzyl)-N,N-bis[3-(dimethylamino)propyl]amine substituent | 849.43 | 849.3 | E | I |

TABLE 1-continued
5"-Allyl Derivatives
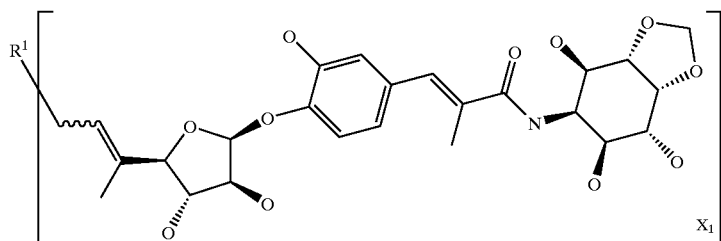
| Example | R1 | MW(Calc.) | MW(Obs) | E/Z | method |
|---|---|---|---|---|---|
| 174 | | 820.39 | 820.3 | E | I |
| 175 | | 834.41 | 834.3 | E | I |
| 176 | | 818.37 | 818.4 | E | I |

TABLE 1-continued
5"-Allyl Derivatives
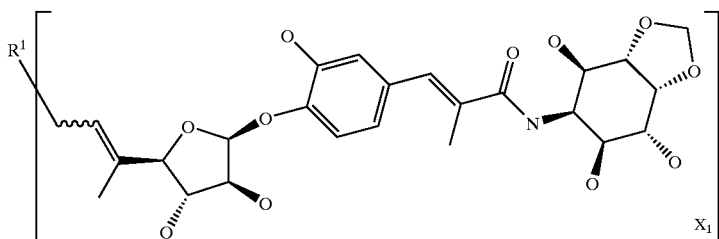
| Example | R1 | MW(Calc.) | MW(Obs) | E/Z | method |
|---|---|---|---|---|---|
| 177 | | 860.45 | 860.4 | E | I |
| 178 | | 820.39 | 820.5 | E | I |
| 179 | | 846.42 | 846.3 | E | I |

TABLE 1-continued
5"-Allyl Derivatives
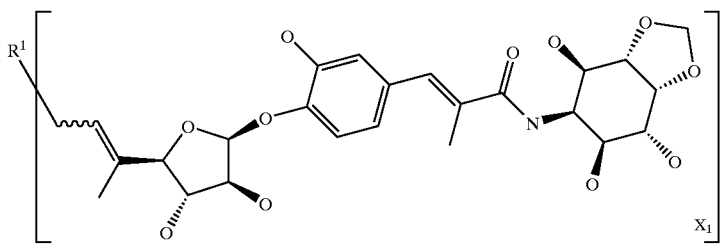
| Example | R1 | MW(Calc.) | MW(Obs) | E/Z | method |
|---|---|---|---|---|---|
| 180 | | 818.37 | 818 | E | I |
| 181 | | 844.41 | 844.1 | E | I |
| 182 | | 846.42 | 845.9 | E | I |

TABLE 1-continued

5"-Allyl Derivatives

| Example | R1 | MW(Calc.) | MW(Obs) | E/Z | method |
|---|---|---|---|---|---|
| 183 | (3-chloro-4-O-X1-benzyl)(cyclopropylmethyl)(3-pyrrolidin-1-ylpropyl)amine | 830.38 | 830.1 | E | I |
| 184 | (5-chloro-2-fluoro-4-O-X1-benzyl)(benzyl)(3-pyrrolidin-1-ylpropyl)amine | 884.4 | 884 | E | I |
| 185 | (3-chloro-4-O-X1-benzyl)(isopropyl)(2-pyrrolidin-1-ylethyl)amine | 818.37 | 818.2 | E | I |

TABLE 1-continued

5"-Allyl Derivatives

| Example | R1 | MW(Calc.) | MW(Obs) | E/Z | method |
|---|---|---|---|---|---|
| 186 | (2-chloro-5-fluoro-4-{[isopropyl(2-pyrrolidin-1-ylethyl)amino]methyl}phenyl) | 836.36 | 836.1 | E | I |
| 187 | (2,3-dichloro-4-{[benzyl(2-pyrrolidin-1-ylethyl)amino]methyl}phenyl) | 900.86 | 900.7 | E | J |
| 188 | (2,3-dichloro-4-{[isobutyl(2-pyrrolidin-1-ylethyl)amino]methyl}phenyl) | 866.84 | 867.8 | E | J |

TABLE 1-continued
5"-Allyl Derivatives
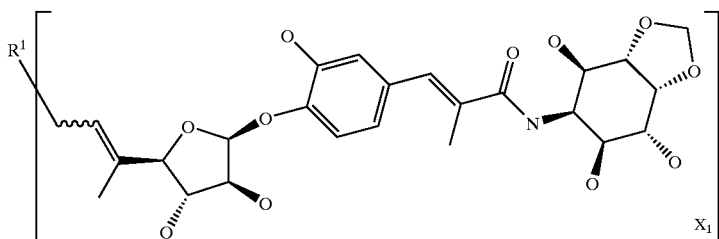
| Example | R1 | MW(Calc.) | MW(Obs) | E/Z | method |
|---|---|---|---|---|---|
| 189 | | 838.79 | 837.9 | E | J |
| 190 | | 784.27 | 783.9 | E | J |
| 191 | | 777.27 | 777.1 | E | J |

TABLE 1-continued
5"-Allyl Derivatives
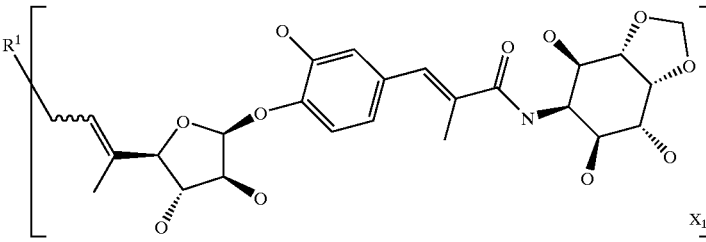
| Example | R1 | MW(Calc.) | MW(Obs) | E/Z | method |
|---|---|---|---|---|---|
| 192 | 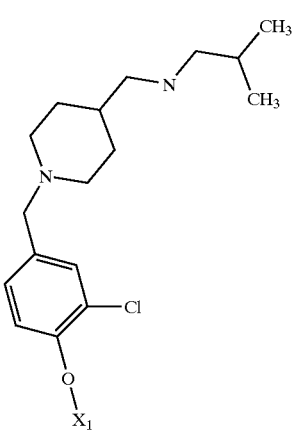 | 832.4 | 832.1 | E | J |
| 193 | 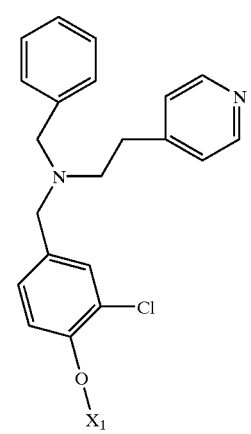 | 832.4 | 831.8 | E | J |
| 194 |  | 874.39 | 874 | E | J |

TABLE 1-continued
5"-Allyl Derivatives
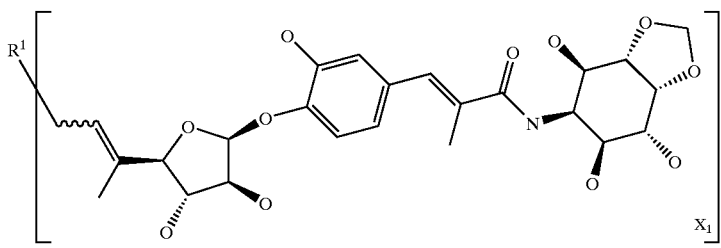
| Example | R1 | MW(Calc.) | MW(Obs) | E/Z | method |
|---|---|---|---|---|---|
| 195 | | 838.36 | 837.9 | E | Pd |
| 196 | | 852.39 | 852.4 | E | I |
| 197 | | 791.26 | 791.3 | E | I |
| 198 | | 770.24 | 770.6 | E | I |

TABLE 1-continued
5"-Allyl Derivatives
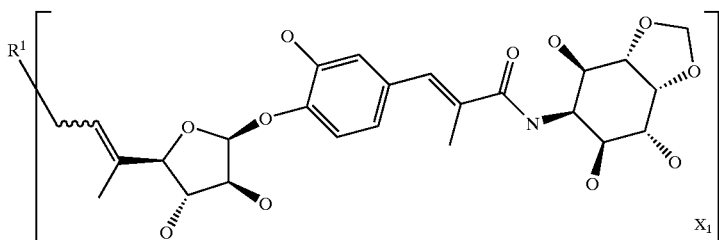
| Example | R1 | MW(Calc.) | MW(Obs) | E/Z | method |
|---|---|---|---|---|---|
| 199 | (indol-3-yl-ethyl)-N-(3-chloro-4-O-X₁-benzyl) | 822.32 | 822.6 | E | I |
| 200 | cycloheptyl-N-(3-chloro-4-O-X₁-benzyl) | 775.3 | 775.3 | E | I |
| 201 | isopentyl-N-(3-chloro-4-O-X₁-benzyl) | 749.26 | 749.3 | E | I |
| 202 | (5-methoxyindol-3-yl-ethyl)-N-(3-chloro-4-O-X₁-benzyl) | 852.34 | 852.4 | E | I |
| 203 | (3-phenylpropyl)-N-(3-chloro-4-O-X₁-cyclohexyl) | 797.31 | 798.9 | E | I |

TABLE 1-continued
5"-Allyl Derivatives
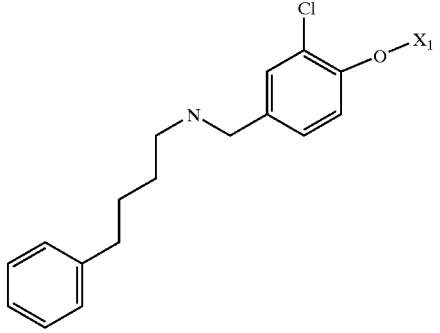
| Example | R1 | MW(Calc.) | MW(Obs) | E/Z | method |
|---|---|---|---|---|---|
| 204 | 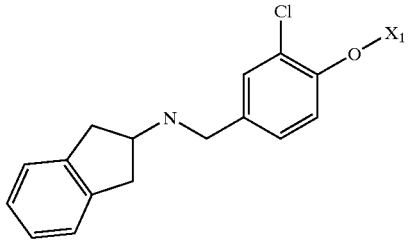 | 811.33 | 811.4 | E | I |
| 205 | 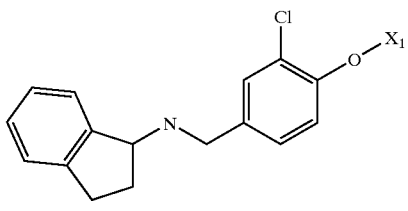 | 795.29 | 783.3 | E | I |
| 206 | 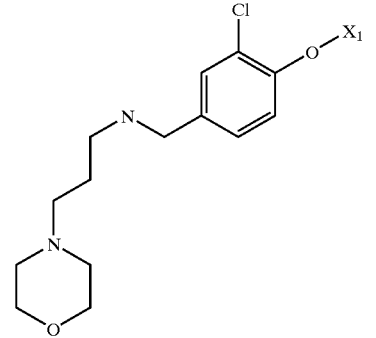 | 795.29 | 795.3 | E | I |
| 207 |  | 806.32 | 806.4 | E | I |

TABLE 1-continued
5"-Allyl Derivatives
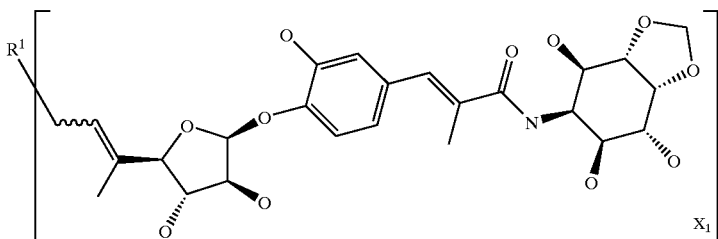
| Example | R1 | MW(Calc.) | MW(Obs) | E/Z | method |
|---------|----|-----------|---------|-----|--------|
| 208 | | 813.26 | 813.3 | E | I |
| 209 | | 819.36 | 819.4 | E | I |
| 210 | | 792.33 | 792.7 | E | I |
| 211 | | 804.3 | 804.4 | E | I |

TABLE 1-continued
5"-Allyl Derivatives
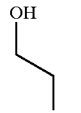
| Example | R1 | MW(Calc.) | MW(Obs) | E/Z | method |
|---|---|---|---|---|---|
| 212 | 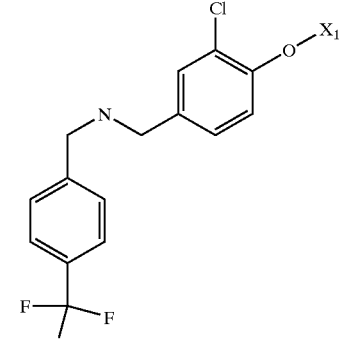 | 824.33 | 824.4 | E | I |
| 213 | 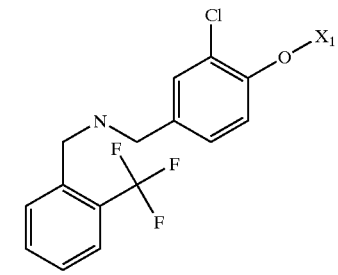 | 837.25 | 837.3 | E | I |
| 214 | 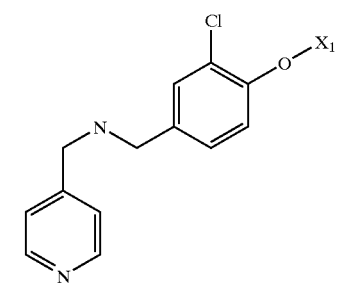 | 837.25 | 837.3 | E | I |
| 215 | | 770.24 | 770.3 | E | I |

TABLE 1-continued
5″-Allyl Derivatives
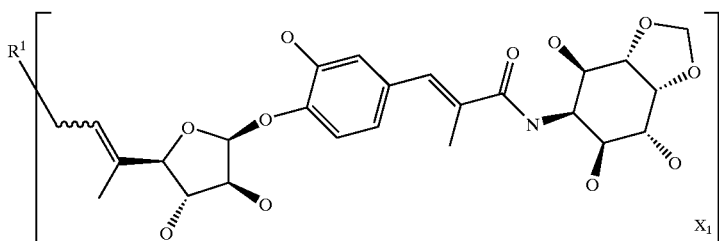
| Example | R1 | MW(Calc.) | MW(Obs) | E/Z | method |
|---|---|---|---|---|---|
| 216 | | 817.73 | 819 | E | I |
| 217 | | 825.36 | 825.4 | E | I |
| 218 | | 835.26 | 835.5 | E | I |
| 219 | | 721.21 | 721.3 | E | I |

US 6,867,230 B2
141                                                                                             142
TABLE 1-continued
5"-Allyl Derivatives
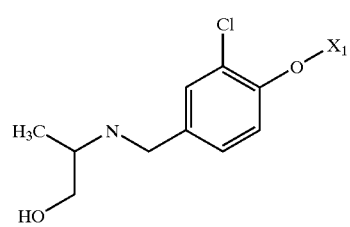
| Example | R1 | MW(Calc.) | MW(Obs) | E/Z | method |
|---|---|---|---|---|---|
| 220 | 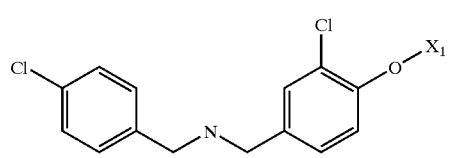 | 737.21 | 737.3 | E | I |
| 221 | 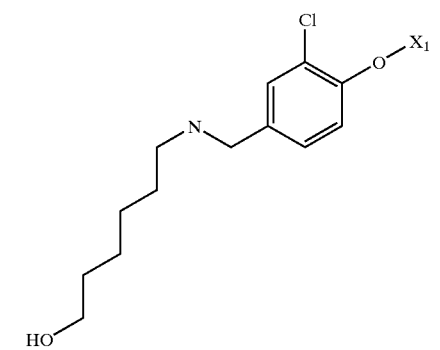 | 803.7 | 804.9 | E | I |
| 222 | 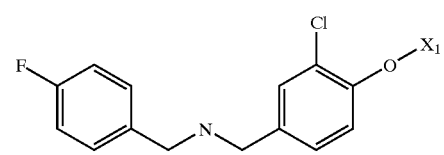 | 779.29 | 779.3 | E | I |
| 223 | 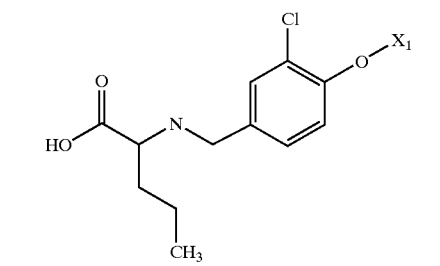 | 787.24 | 787.3 | E | I |
| 224 | | 779.24 | 779.3 | E | I |

TABLE 1-continued
5″-Allyl Derivatives
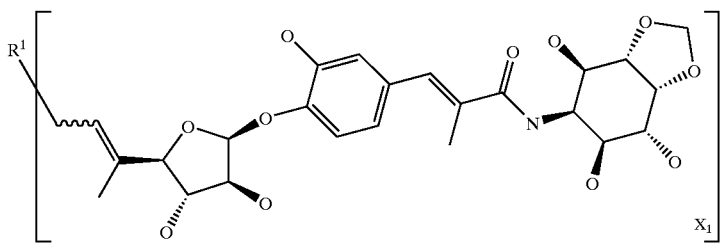
| Example | R1 | MW(Calc.) | MW(Obs) | E/Z | method |
|---|---|---|---|---|---|
| 225 | (3-chloro-4-O-X₁-benzyl)(furan-2-ylmethyl)amine | 759.21 | 759.3 | E | I |
| 226 | (3-chloro-4-O-X₁-benzyl)(3-methoxypropyl)amine | 751.24 | 751.3 | E | I |
| 227 | (3-chloro-4-O-X₁-benzyl)(1,3-dioxolan-2-ylmethyl)amine | 765.22 | 765.3 | E | I |
| 228 | (3-chloro-4-O-X₁-benzyl)(3-hydroxypropyl)amine | 737.21 | 737.3 | E | I |
| 229 | (3-chloro-4-O-X₁-benzyl)(cyclohexyl)amine | 761.27 | 761.3 | E | I |

TABLE 1-continued
5"-Allyl Derivatives
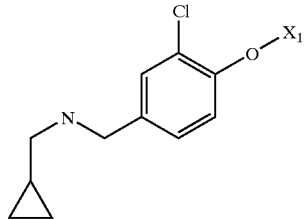
| Example | R1 | MW(Calc.) | MW(Obs) | E/Z | method |
|---|---|---|---|---|---|
| 230 | 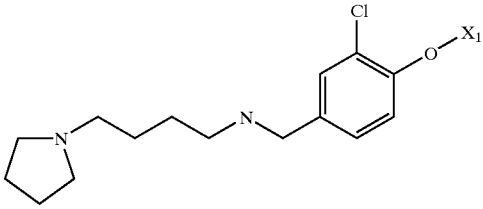 | 733.22 | 733.3 | E | I |
| 231 | 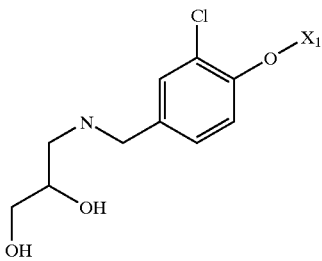 | 804.34 | 804.7 | E | I |
| 232 | 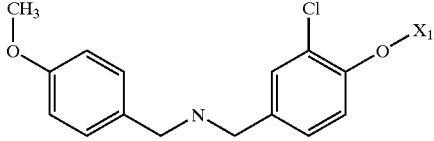 | 753.21 | 753.7 | E | I |
| 233 | 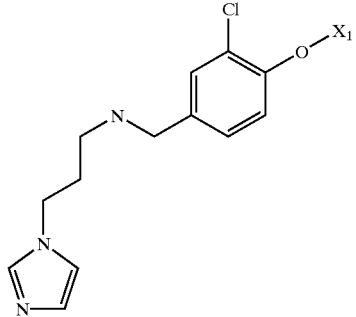 | 799.28 | 799.3 | E | I |
| 234 | | 787.27 | 787.6 | E | I |

TABLE 1-continued
5''-Allyl Derivatives
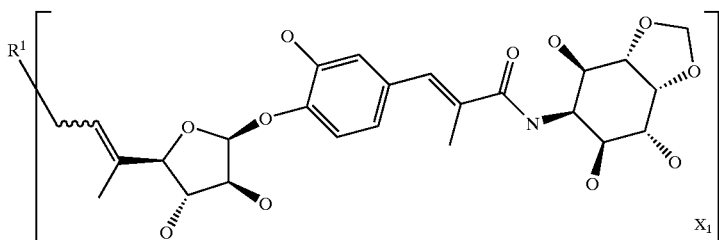
| Example | R1 | MW(Calc.) | MW(Obs) | E/Z | method |
|---|---|---|---|---|---|
| 235 | | 811.29 | 811.3 | E | I |
| 236 | | 806.32 | 806.4 | E | I |
| 237 | | 843.33 | 843.4 | E | I |
| 238 | | 784.27 | 784.3 | E | I |

TABLE 1-continued
5"-Allyl Derivatives
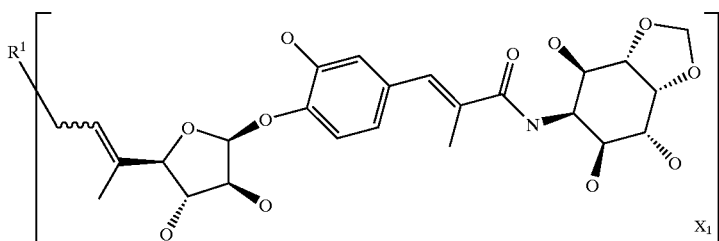
| Example | R1 | MW(Calc.) | MW(Obs) | E/Z | method |
|---|---|---|---|---|---|
| 239 | | 788.3 | 788.3 | E | I |
| 240 | | 813.31 | 813.3 | E | I |
| 241 | | 790.32 | 790.3 | E | I |
| 242 | | 881.43 | 881.4 | E | I |
| 243 | | 791.3 | 792.9 | E | I |

TABLE 1-continued
5''-Allyl Derivatives
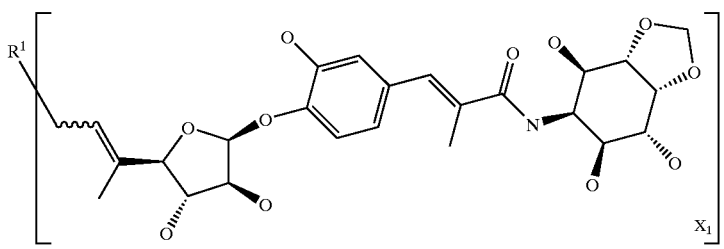
| Example | R1 | MW(Calc.) | MW(Obs) | E/Z | method |
|---|---|---|---|---|---|
| 244 | | 765.26 | 765.3 | E | I |
| 245 | | 778.3 | 778.6 | E | I |
| 246 | | 764.28 | 764.4 | E | I |
| 247 | | 820.39 | 820.4 | E | I |
| 248 | | 817.73 | 819 | E | I |

TABLE 1-continued

5"-Allyl Derivatives

| Example | R1 | MW(Calc.) | MW(Obs) | E/Z | method |
|---------|----|-----------|---------|-----|--------|
| 249 | | 764.28 | 764.3 | E | I |
| 250 | | 838.14 | 839 | E | I |
| 251 | | 779.29 | 779.4 | E | I |
| 252 | | 747.25 | 746.7 | E | I |
| 253 | | 770.24 | 770.3 | E | I |

TABLE 1-continued
5''-Allyl Derivatives
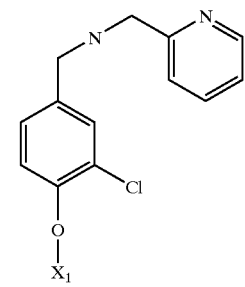
| Example | R1 | MW(Calc.) | MW(Obs) | E/Z | method |
|---|---|---|---|---|---|
| 254 | 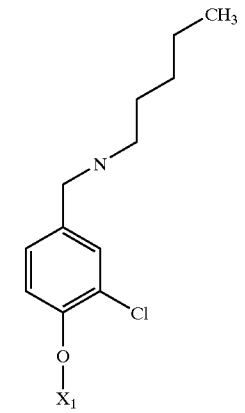 | 770.24 | 769.8 | E | I |
| 255 | 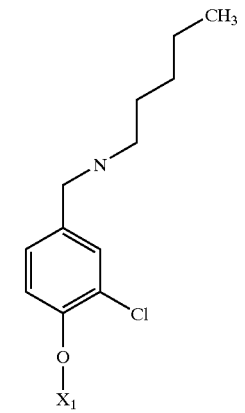 | 749.26 | 749.3 | E | I |
| 256 | | 749.26 | 749.6 | E | I |

TABLE 1-continued
5"-Allyl Derivatives
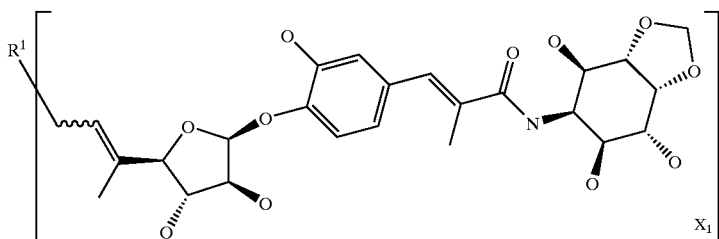
| Example | R1 | MW(Calc.) | MW(Obs) | E/Z | method |
|---|---|---|---|---|---|
| 257 | 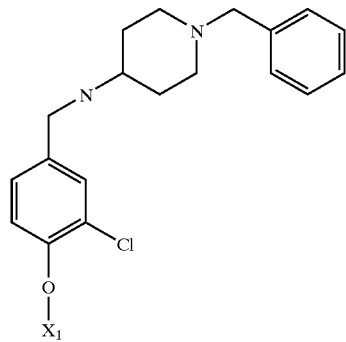 | 852.39 | 852.7 | E | I |
| 258 | 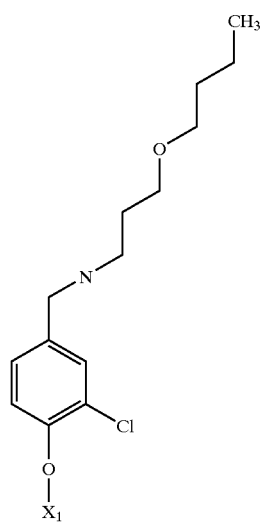 | 793.32 | 793.4 | E | I |

TABLE 1-continued
5"-Allyl Derivatives
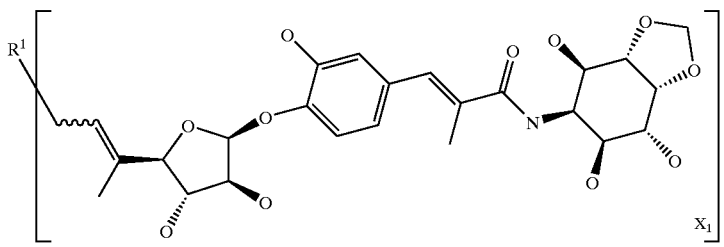
| Example | R1 | MW(Calc.) | MW(Obs) | E/Z | method |
|---------|----|-----------|---------|-----|--------|
| 259 | | 793.32 | 790.3 | E | I |
| 260 | | 790.32 | 790.3 | E | I |
| 261 | | 747.25 | 747.3 | E | I |

TABLE 1-continued
5"-Allyl Derivatives
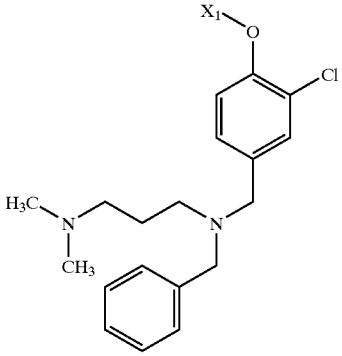
| Example | R1 | MW(Calc.) | MW(Obs) | E/Z | method |
|---|---|---|---|---|---|
| 262 | 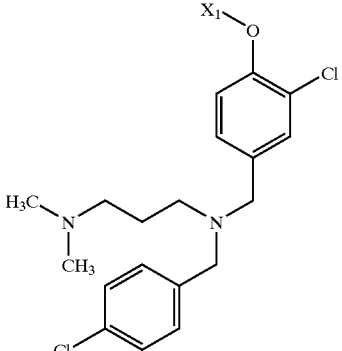 | 854.4 | 854.3 | E | I |
| 263 | | 888.85 | 888.2 | E | I |
| 264 | 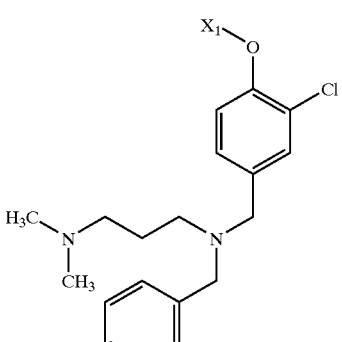 | 884.43 | 884.2 | E | I |

TABLE 1-continued

5"-Allyl Derivatives

| Example | R1 | MW(Calc.) | MW(Obs) | E/Z | method |
|---------|----|-----------|---------|-----|--------|
| 265 | [3-chloro-4-(X₁-O)benzyl][(4-fluorobenzyl)][3-(dimethylamino)propyl]amine | 872.39 | 872.2 | E | I |
| 266 | [3-chloro-4-(X₁-O)benzyl][(3,4-dichlorobenzyl)][3-(dimethylamino)propyl]amine | 923.29 | 922 | E | I |
| 267 | [3-chloro-4-(X₁-O)benzyl][(3,4-difluorobenzyl)][3-(dimethylamino)propyl]amine | 890.36 | 890.2 | E | I |

TABLE 1-continued
5"-Allyl Derivatives
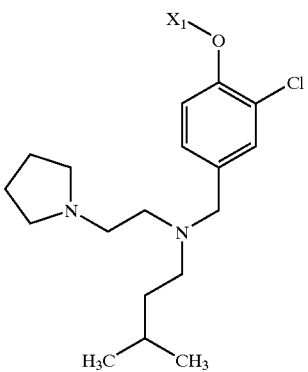
| Example | R1 | MW(Calc.) | MW(Obs) | E/Z | method |
|---|---|---|---|---|---|
| 268 | 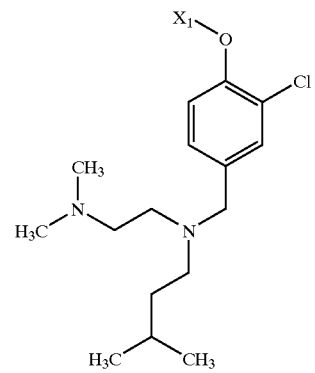 | 846.42 | 846.3 | E | I |
| 269 | 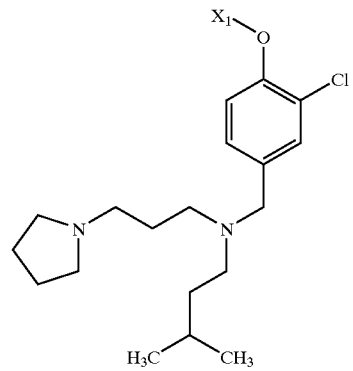 | 820.39 | 820.3 | E | I |
| 270 |  | 860.45 | 860.3 | E | I |

TABLE 1-continued
5"-Allyl Derivatives
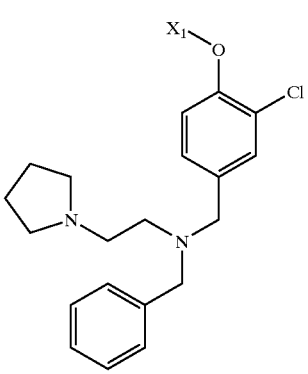
| Example | R1 | MW(Calc.) | MW(Obs) | E/Z | method |
|---|---|---|---|---|---|
| 271 | 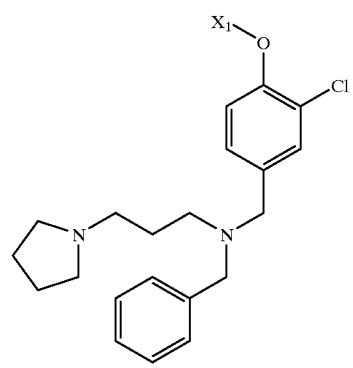 | 866.41 | 866.2 | E | I |
| 272 | | 879.45 | 880.1 | E | I |
| 273 | 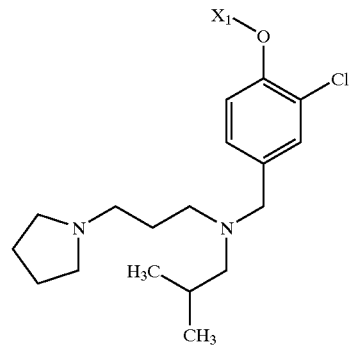 | 846.42 | 846.2 | E | I |

TABLE 1-continued
5"-Allyl Derivatives
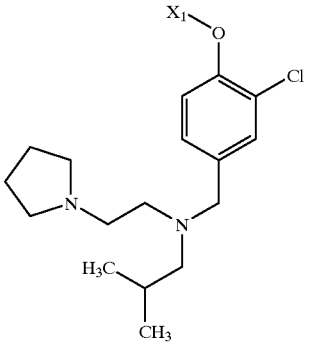
| Example | R1 | MW(Calc.) | MW(Obs) | E/Z | method |
|---|---|---|---|---|---|
| 274 | 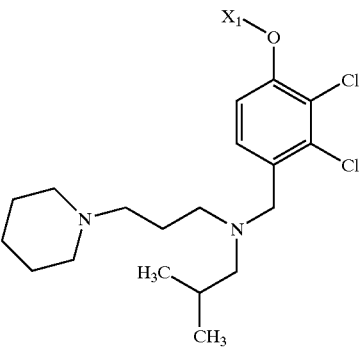 | 832.4 | 832 | E | I |
| 275 | | 894.9 | 894.1 | E | J |
| 276 | 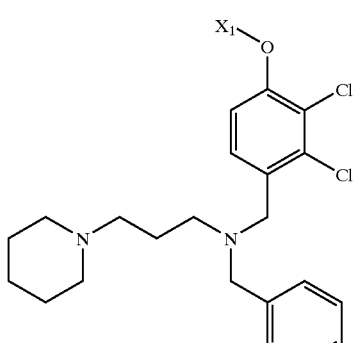 | 928.9 | 928 | E | J |

TABLE 1-continued
5"-Allyl Derivatives
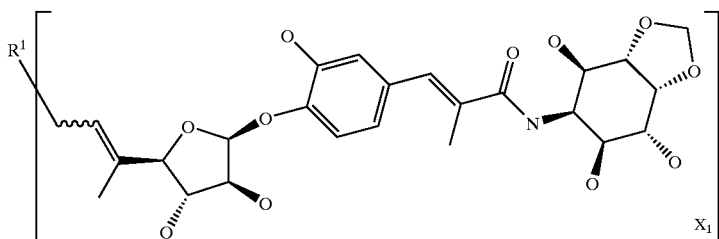
| Example | R1 | MW(Calc.) | MW(Obs) | E/Z | method |
|---|---|---|---|---|---|
| 277 | | 832.4 | 832.4 | E | J |
| 278 | | 924.45 | 924.2 | E | I |
| 279 | | 784.27 | 784.3 | E | I |

TABLE 1-continued
5″-Allyl Derivatives
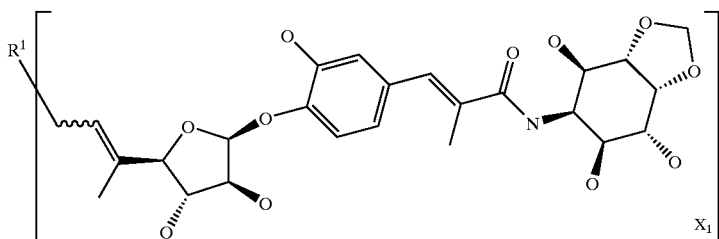
| Example | R1 | MW(Calc.) | MW(Obs) | E/Z | method |
| --- | --- | --- | --- | --- | --- |
| 280 | (3-O-X₁-benzyl)-N-methyl-N-(2-(N-methyl-N-benzylamino)ethyl)amine | 805.93 | 806.3 | E:Z mix | I |
| 281 | (2-chloro-3-O-X₁-benzyl)-N-methyl-N-(2-(N-methyl-N-benzylamino)ethyl)amine | 840.37 | 840.4 | E:Z mix | I |
| 282 | (3-O-X₁-benzyl)-N-methyl-N-(2-(pyridin-4-yl)ethyl)amine | 763.84 | 764.2 | E:Z mix | I |
| 283 | (3-O-X₁-benzyl)-N-benzyl-N-(2-(N,N-dimethylamino)ethyl)amine | 805.93 | 806.3 | E:Z mix | I |

TABLE 1-continued
5"-Allyl Derivatives
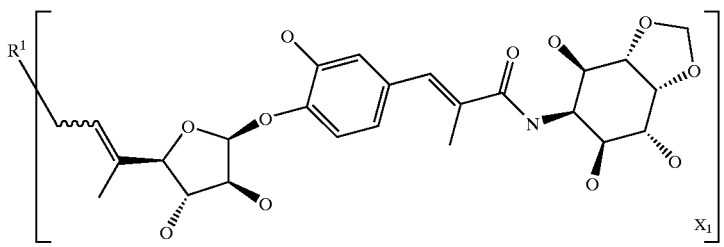
| Example | R1 | MW(Calc.) | MW(Obs) | E/Z | method |
|---|---|---|---|---|---|
| 284 | | 840.37 | 840.2 | E:Z mix | I |
| 285 | | 840.37 | 840.3 | E:Z mix | I |
| 286 | | 798.29 | 798.2 | E:Z mix | I |
| 287 | | 792.33 | 792.2 | E:Z mix | I |

TABLE 1-continued
5"-Allyl Derivatives
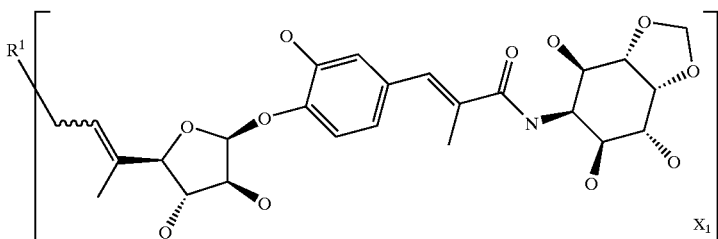
| Example | R1 | MW(Calc.) | MW(Obs) | E/Z | method |
|---|---|---|---|---|---|
| 288 | | 840.38 | 840.3 | E:Z mix | I |
| 289 | | 798.29 | 798.2 | E:Z mix | I |
| 290 | | 757.88 | 758.2 | E:Z mix | I |
| 291 | | 729.83 | 730.3 | E:Z mix | I |
| 292 | | 743.85 | 744.2 | E:Z mix | I |

TABLE 1-continued

5"-Allyl Derivatives

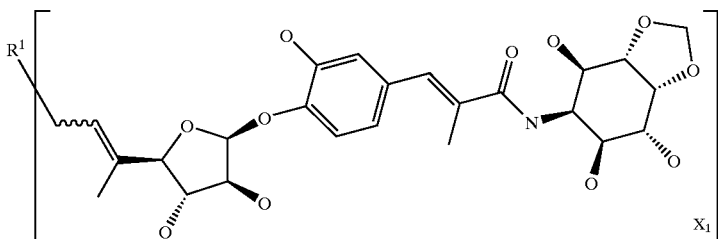

| Example | R1 | MW(Calc.) | MW(Obs) | E/Z | method |
|---|---|---|---|---|---|
| 293 | (3-methyl-N-(2-dimethylaminoethyl)-N-methylaminomethyl-2-chlorophenoxy) | 764.27 | 764.3 | E:Z mix | I |
| 294 | (3-(N-(3-(N-ethyl-N-methylamino)propyl)-N-methylaminomethyl)-2-chlorophenoxy) | 792.33 | 792.2 | E:Z mix | I |
| 295 | (4-(N-methyl-N-(2-(pyridin-4-yl)ethyl)aminomethyl)phenoxy) | 763.84 | 764.3 | E:Z mix | I |
| 296 | (4-(N-ethyl-N-(3-dimethylaminopropyl)aminomethyl)phenoxy) | 757.89 | 758.4 | E:Z mix | I |
| 297 | (4-(N-methyl-N-(2-(N-methyl-N-benzylamino)ethyl)aminomethyl)phenoxy) | 805.93 | 806.2 | E:Z mix | I |

TABLE 1-continued
5"-Allyl Derivatives
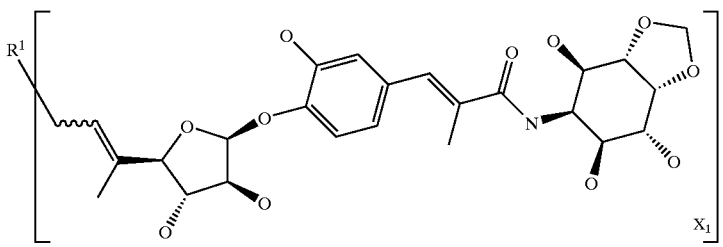
| Example | R1 | MW(Calc.) | MW(Obs) | E/Z | method |
|---|---|---|---|---|---|
| 298 | 3-chloro-4-(OX₁)-benzyl-N(CH₃)CH₂CH₂N(CH₃)₂ | 764.28 | 764.4 | E:Z mix | I |
| 299 | 4-(OX₁)-benzyl-N(CH₃)CH₂CH₂N(CH₃)₂ | 729.83 | 730.3 | E:Z mix | I |
| 300 | 2-chloro-3-(OX₁)-benzyl-piperidine | 747.24 | 747.4 | E | H |
| 301 | 2-chloro-3-(OX₁)-benzyl-N(CH₃)CH₂CH₂N(CH₃)₂ | 750.25 | 750.3 | E | H |
| 302 | 2-chloro-3-(OX₁)-benzyl-N(CH₃)CH₂CH(CH₃)₂ | 749.26 | 749.3 | E | H |

TABLE 1-continued

5"-Allyl Derivatives

| Example | R1 | MW(Calc.) | MW(Obs) | E/Z | method |
|---|---|---|---|---|---|
| 303 | 2-chloro-3-((4-methylpiperazin-1-yl)methyl)phenyl-O-X₁ | 762.26 | 762.2 | E | I |
| 304 | 2-chloro-3-(pyrrolidin-1-ylmethyl)phenyl-O-X₁ | 733.21 | 733.2 | E | I |
| 305 | 2-chloro-3-((cyclopentylamino)methyl)phenyl-O-X₁ | 747.24 | 747.1 | E | H |
| 306 | 2-chloro-3-((cyclohexylamino)methyl)phenyl-O-X₁ | 761.27 | 761.1 | E | H |
| 307 | 2-chloro-3-((4-phenylpiperazin-1-yl)methyl)phenyl-O-X₁ | 824.33 | 824.1 | E | I |

TABLE 1-continued

5″-Allyl Derivatives

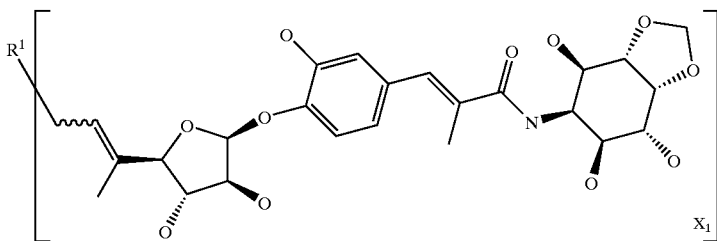

| Example | R1 | MW(Calc.) | MW(Obs) | E/Z | method |
|---|---|---|---|---|---|
| 308 | 3-(4-hydroxypiperidin-1-ylmethyl)-2-chlorophenoxy | 763.24 | 763.1 | E | I |
| 309 | 3-(4-benzylpiperazin-1-ylmethyl)-2-chlorophenoxy | 838.36 | 838.1 | E | I |
| 310 | 3-[4-(3-hydroxypropyl)piperazin-1-ylmethyl]-2-chlorophenoxy | 806.31 | 806.1 | E | I |
| 311 | 4-(4-carbamoylpiperidin-1-ylmethyl)-2-chlorophenoxy | 790.27 | 790 | E | I |
| 312 | 3-{[3-(imidazol-1-yl)propylamino]methyl}-2-chlorophenoxy | 787.27 | 787.3 | E | I |
| 313 | 3-{[3-(dimethylamino)propylamino]methyl}-2-chlorophenoxy | 764.27 | 764 | E | I |

TABLE 1-continued
5''-Allyl Derivatives
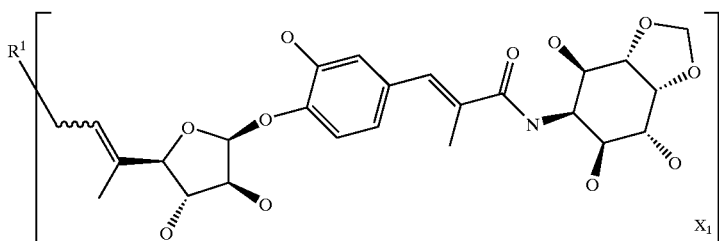
| Example | R1 | MW(Calc.) | MW(Obs) | E/Z | method |
|---|---|---|---|---|---|
| 314 | | 792.33 | 791.7 | E | I |
| 315 | | 860.36 | 860.3 | E | I |
| 316 | | 846.42 | 844.3 | E | I |
| 317 | | 896.48 | 896.4 | E | I |

TABLE 1-continued

5"-Allyl Derivatives

| Example | R1 | MW(Calc.) | MW(Obs) | E/Z | method |
|---|---|---|---|---|---|
| 318 | | 919.26 | 918.1 | E | I |
| 319 | | 852.38 | 852.3 | E | I |
| 320 | | 826.34 | 826 | E | I |
| 321 | | 719.192 | 719.1 | E | H |

TABLE 1-continued

5''-Allyl Derivatives

| Example | R1 | MW(Calc.) | MW(Obs) | E/Z | method |
|---------|----|-----------|---------|-----|--------|
| 322 | | 810.73 | 809.8 | E | H |
| 323 | | 812.3 | 812.3 | E | |
| 324 | | 826.3 | 826.3 | E | |

TABLE 2
5"-Allyl-2"-Deoxy Derivatives (Examples 325–333)
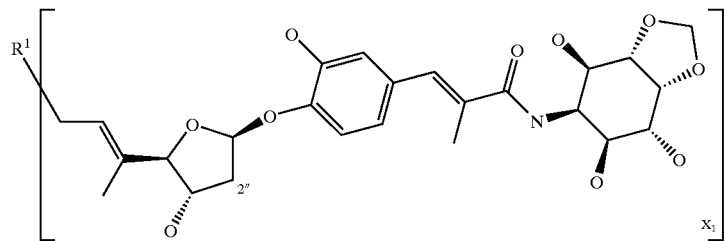
| Example # | R1 | MW | MS (obs) | E/Z | Method |
|---|---|---|---|---|---|
| 325 | 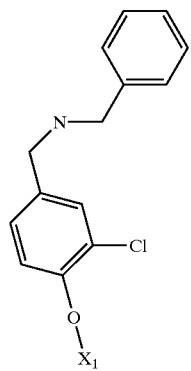 | 753.25 | 753.2 | E | I |
| 326 | 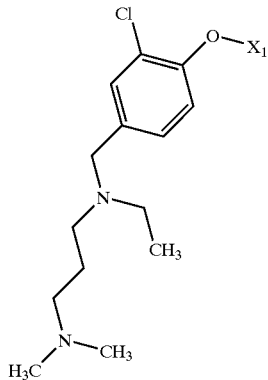 | 776.33 | 776.3 | E | I |
| 327 | 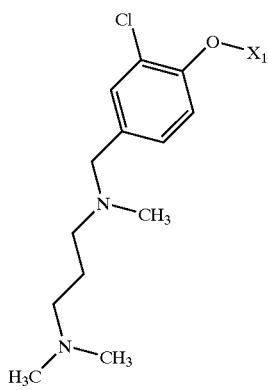 | 762.3 | 762.3 | E | I |

TABLE 2-continued
5"-Allyl-2"-Deoxy Derivatives (Examples 325–333)
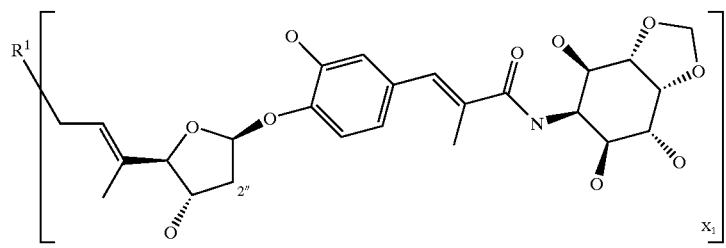
| Example # | R1 | MW | MS (obs) | E/Z | Method |
|---|---|---|---|---|---|
| 328 | | 691.18 | 691.2 | E | I |
| 329 | | 824.38 | 824.3 | E | I |
| 330 | | 762.3 | 762.3 | E | J |

TABLE 2-continued
5"-Allyl-2"-Deoxy Derivatives (Examples 325–333)
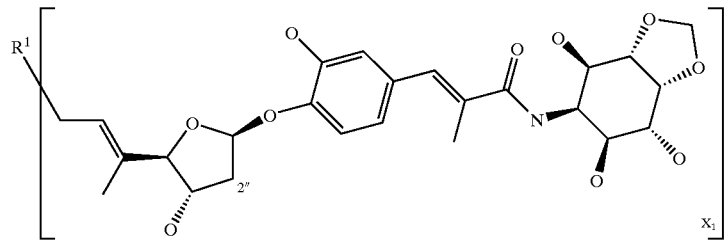
| Example # | R1 | MW | MS (obs) | E/Z | Method |
|---|---|---|---|---|---|
| 331 | | 691.14 | 691.1 | E | I |
| 332 | | 782.3 | 782.2 | E | I |
| 333 | | 748.28 | 748.3 | E | I |

TABLE 3
5"-Allyl-3-Deoxy Derivative Preparation (Example 334–342)
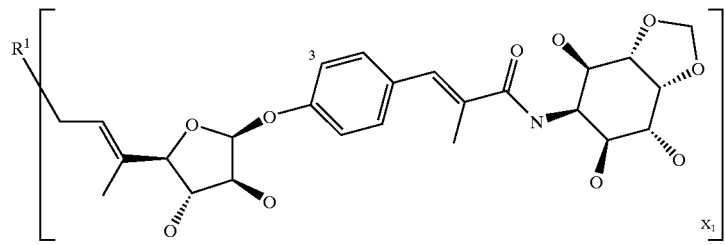
| Example # | R1 | MW | MS (obs) | E/Z | Method |
|---|---|---|---|---|---|
| 334 | | 753.25 | 753.2 | E | I |
| 335 | | 776.33 | 776.2 | E | I |
| 336 | | 748.28 | 748.2 | E | I |

TABLE 3-continued
5"-Allyl-3-Deoxy Derivative Preparation (Example 334–342)
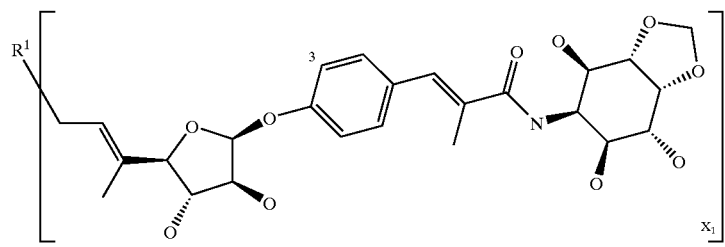
| Example # | R1 | MW | MS (obs) | E/Z | Method |
|---|---|---|---|---|---|
| 337 | 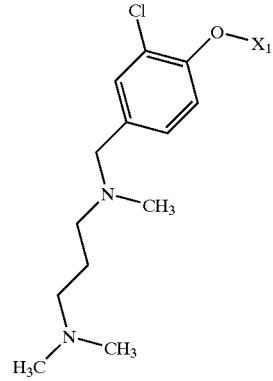 | 762.3 | 762.4 | E | I |
| 338 | 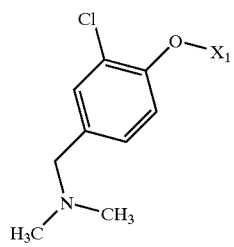 | 691.18 | 691.3 | E | I |
| 339 | 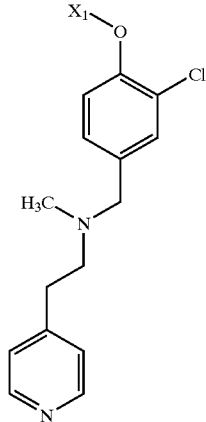 | 782.3 | 782.2 | E | I |

TABLE 3-continued
5"-Allyl-3-Deoxy Derivative Preparation (Example 334–342)
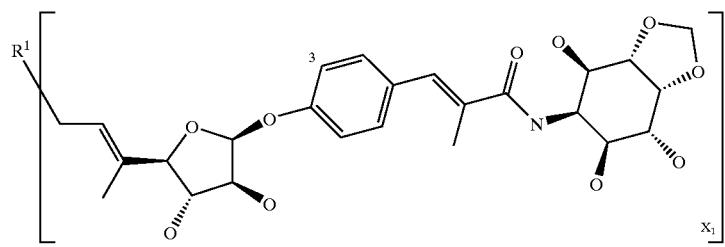
| Example # | R1 | MW | MS (obs) | E/Z | Method |
|---|---|---|---|---|---|
| 340 | 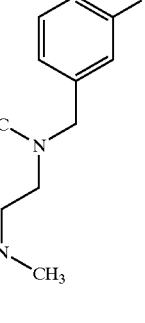 | 824.38 | 824.2 | E | I |
| 341 | 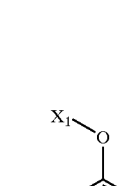 | 824.28 | 824.2 | E | I |
| 342 | 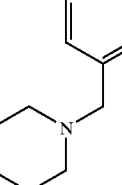 | 768.27 | 768.3 | E | I |

Each of the above compounds that were made, or can be made, according to the synthetic methods described above fall within the scope of the present invention. Further, the compounds referred to in the table above also fall within the scope of the present invention.

What is claimed is:

1. A compound of the formula

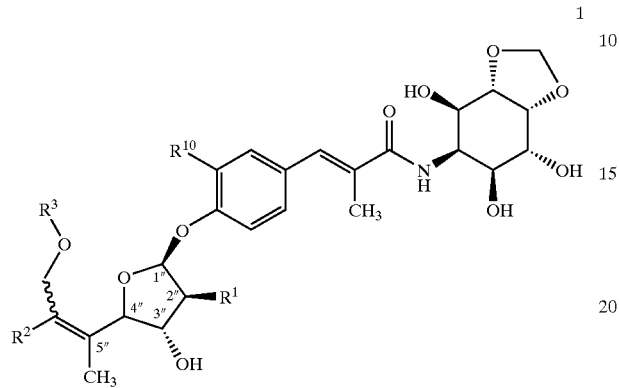

or a pharmaceutically acceptable prodrug, salt or solvate thereof wherein:

$R^1$ and $R^{10}$ are each independently H or OH;

$R^2$ is H or $C_1$–$C_6$ alkyl wherein the foregoing $R^2$ alkyl group is optionally substituted by 1 or 2 $R^4$ groups;

$R^3$ is independently selected from $C_1$–$C_{10}$ aryl or 5 to 10 membered heteroaromatic, and the heteroaromatic and aryl moieties of the foregoing $R^3$ groups are substituted by a —$CHR^9NR^{11}R^{12}$ group and optionally substituted by 1 to 4 $R^4$ groups;

$R^4$ is independently selected from, $C_1$–$C_{10}$ alkyl, $C_2$–$C_{10}$ alkenyl, $C_2$–$C_{10}$ alkynyl, halo, cyano, nitro, trifluoromethyl, difluoromethyl, trifluoromethoxy, azido, hydroxy, $C_1$–$C_6$ alkoxy, —$C(O)R^5$, —$C(O)OR^5$, —$NR^6C(O)OR^8$, —$OC(O)R^5$, —$NR^6SO_2R^8$, —$SO_2NR^5R^6$, —$NR^6C(O)R^5$, —$C(O)NR^5R^6$, —$NR^5R^6$, —$S(O)_j(CR^6R^7)_m(C_6$–$C_{10}$ aryl), —$S(O)_j$ ($C_1$–$C_6$ alkyl), —$(CR^6R^7)_m(C_6$–$C_{10}$ aryl), —$O(CR^6 R^7)_m(C_6$–$C_{10}$ aryl), —$NR^6(CR^6R^7)_m(C_6$–$C_{10}$ aryl), —$(CR^6R^7)_m$(4 to 10 membered heterocyclic), —$C(O)$ $(CR^6R^7)_m(C_6$–$C_{10}$ aryl), and —$C(O)(CR^6R^7)_m$(4 to 10 membered heterocyclic), wherein m is an integer from 0 to 4; j is an integer from 0 to 2, and said alkyl, alkenyl, alkynyl, aryl and heterocyclic moieties of the foregoing $R^4$ groups are optionally substituted by 1 to 3 substituents independently selected from halo, cyano, nitro, trifluoromethyl, trifluoromethoxy, azido, —$NR^6SO_2R^8$, —$SO_2NR^5R^6$, —$C(O)R^5$, —$C(O)OR^5$, —$OC(O)R^5$, —$NR^6C(O)OR^8$, —$NR^6C(O)R^5$, —$C(O)$ $NR^5R^6$, —$NR^5R^6$, —$OR^5$, $C_1$–$C_{10}$ alkyl, —$(CR^6R^7)_m$ ($C_6$–$C_{10}$ aryl), and —$(CR^6R^7)_m$(4 to 10 membered heterocyclic), wherein m is an integer from 0 to 4;

each $R^5$, $R^9$, $R^{11}$, $R^{12}$, $R^{13}$ and $R^{14}$ is independently selected from H, $C_1$–$C_{10}$ alkyl, —$(CR^6R^7)_m(C_6$–$C_{10}$ aryl), —$(CR^6R^7)_m(C_3$–$C_{10}$cycloalkyl), indanyl and —$(CR^6R^7)_m$(4 to 10 membered heterocyclic), wherein m is an integer from 0 to 4, and the foregoing $R^5$, $R^{11}$, $R^9$ and $R^{12}$ substituents, except H, are optionally substituted by 1 to 3 substituents independently selected from halo, cyano, nitro, benzyl, trifluoromethyl, trifluoromethoxy, azido, —$CH_2(C_2$–$C_6$ alkenyl), —$C(O)R^6$, —$C(O)OR^6$, —$OC(O)R^6$, —$NR^6C(O)R^7$, —$C(O)NR^6R^7$, —$NR^6R^7$, hydroxy, $C_1$–$C_6$ alkyl, and $C_1$–$C_6$ alkoxy;

or $R^{11}$ and $R^{12}$ can be taken together to form a 4 to 7 membered heterocyclic group optionally substituted by one $R^{14}$ group;

$R^6$ and $R^7$ are each independently selected from H, —$C(O)(C_1$–$C_6$ alkyl), $C_1$–$C_6$ alkyl or —$(CH_2)_n$ ($C_6$–$C_{10}$ aryl) wherein n is an integer from 0 to 2, and the foregoing aryl substituents are optionally substituted by 1 to 3 substituents independently selected from halo, cyano, nitro, trifluoromethyl, trifluoromethoxy, and azido;

—$NR^6R^7$ can be taken together to form the following structure

and $R^8$ is selected from the substituents provided in the definition of $R^5$ except $R^8$ is not H.

2. A compound acccording to claim 1, wherein $R^3$ is phenyl substituted by one —$CH_2NR^{11}R^{12}$ group and optionally substituted by 1 to 4 $R^4$ groups; and the pharmaceutically acceptable salt, prodrug and solvate of said compound.

3. A compound according to claim 2 wherein said $R^{11}$ and $R^{12}$ groups are each independently selected from $C_1$–$C_{10}$ alkyl, —$(CR^6R^7)_m(C_6$–$C_{10}$ aryl), —$(CR^6R^7)_m(C_3$–$C_{10}$ cycloalkyl), indanyl and —$(CR^6R^7)_m$(4 to 10 membered heterocyclic), wherein m is an integer from 0 to 4, and the foregoing, $R^{11}$ and $R^{12}$ substituents, are optionally substituted by 1 to 3 substituents independently selected from halo, benzyl, trifluoromethyl, trifluoromethoxy, —$NR^6R^7$; and the pharmaceutically acceptable salt, prodrug and solvate of said compound.

4. A compound according to claim 1 wherein one of the $R^4$ group is halo and ortho to the ether oxygen; and the pharmaceutically acceptable salt, prodrug and solvate of said compound.

5. A compound according to claim 4 wherein said halo group is chlorine; and the pharmaceutically acceptable salt, prodrug and solvate of said compound.

6. A compound according to claim 1 wherein said compound is selected from the group consisting of:

3-(4-{(2S,3S,4S,5R)-5-[3-{2-chloro-4-[(methyl-napthalen-1-ylmethyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS, 4R,5R,6S,7R,7aR)-4,6,7-trihydroxy-hexahydro-benzo [1,3]dioxol-5-yl)-(2E)-acrylamide;

3-(4-{(2S,3S,4S,5R)-5-[3-(4-benzylaminomethyl-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(-{(2S,4S,5R)-5-[3-(4-{[Benzyl-(2-dimethylamino-ethyl)-amino]-methyl}-2-chloro-phenoxy)-1-methyl-(1E)-propenyl]-4-hydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide 3-(4-{(2S,3S,4S,5R)-5-[3-(2,3-Dichloro-4-{[(3-dimethylamino-propyl)-ethyl-amino]-methyl}- phenoxy)-1-methyl-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide 3-(4-{(2S,3S,4S,5R)-5-[3-(4-(3-chloro-benzyl)aminomethyl-2-chloro-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-ethylamino-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(3-piperidinyl-2-chloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-benzylaminomethyl-2-chloro-phenoxy)-1-methyl-(1E)-propenyl]-4-hydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-{2-chloro-4-[(benzyl-methyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-{2-chloro-4-[(ethyl-methyl-amino)-methyl]-phenoxy}-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-{2-chloro-4-morpholin-4ylmethyl-phenoxy}-1-methyl-(1E)-propenyl]-3,4-dihydroxy-tetrahydro-furan-2-yloxy}-3-hydroxy-phenyl )-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(4-(3-chloro-benzyl)aminomethyl-2-chloro-phenoxy)-1-methyl-(1E)-propenyl]-3,4-dihydroxy-tetrahydro-furan-2-yloxy}-phenyl )-2-methyl-N-((3aS,4R,5R,6S,7R,7aR)-4,6,7-trihydroxy-hexahydro-benzo[1,3]dioxol-5-yl)-(2E)-acrylamide;

and the pharmaceutically acceptable salts, prodrugs and solvates of said compounds.

7. A pharmaceutical composition for the treatment of a bacterial infection, a protozoal infection, or a disorder related to a bacterial infection or a protozoal infection, in a mammal, fish, or bird which comprises a therapeutically effective amount of a compound, or a pharmaceutically acceptable prodrug, salt or solvate of said compound of claim 1 and a pharmaceutically acceptable carrier.

8. A method of treating a bacterial infection, a protozoal infection, or a disorder related to a bacterial infection or a protozoal infection, in a mammal, fish, or bird which comprises administering to said mammal, fish or bird a therapeutically effective amount of a compound, or a pharmaceutically acceptable prodrug, salt or solvate of said compound of claim 1.

* * * * *